United States Patent
Nakamura et al.

(10) Patent No.: US 9,175,292 B2
(45) Date of Patent: Nov. 3, 2015

(54) APTAMER FOR NGF AND USE THEREOF

(75) Inventors: Yoshikazu Nakamura, Tokyo (JP); Ling Jin, Tokyo (JP); Hisanao Hiramatsu, Osaka (JP)

(73) Assignees: FUJIMOTO PHARMACEUTICAL CORPORATION, Osaka (JP); RIBOMIC INC., Tokyo (JP)

( * ) Notice: Subject to any disclaimer, the term of this patent is extended or adjusted under 35 U.S.C. 154(b) by 0 days.

(21) Appl. No.: 13/636,974

(22) PCT Filed: Mar. 24, 2011

(86) PCT No.: PCT/JP2011/057105
§ 371 (c)(1),
(2), (4) Date: Nov. 15, 2012

(87) PCT Pub. No.: WO2011/118682
PCT Pub. Date: Sep. 29, 2011

(65) Prior Publication Data
US 2013/0052176 A1 Feb. 28, 2013

(30) Foreign Application Priority Data
Mar. 24, 2010 (JP) .................. 2010-068546

(51) Int. Cl.
*C07H 21/02* (2006.01)
*A61K 48/00* (2006.01)
*C12N 15/115* (2010.01)

(52) U.S. Cl.
CPC .......... *C12N 15/115* (2013.01); *C12N 2310/16* (2013.01); *C12N 2310/3515* (2013.01)

(58) Field of Classification Search
None
See application file for complete search history.

(56) References Cited

U.S. PATENT DOCUMENTS

| 5,660,985 A | 8/1997 | Pieken et al. |
| 2010/0004432 A1 | 1/2010 | Miyakawa et al. |
| 2011/0177578 A1 | 7/2011 | Nakamura et al. |

FOREIGN PATENT DOCUMENTS

| WO | WO-91/19813 A1 | 12/1991 |
| WO | WO-94/08050 A1 | 4/1994 |
| WO | WO-95/07364 A1 | 3/1995 |
| WO | WO-02077262 A2 | 10/2002 |
| WO | WO-03/070984 A1 | 8/2003 |
| WO | WO-2004032870 A2 | 4/2004 |
| WO | WO-2004073653 A2 | 9/2004 |
| WO | WO-2004096122 A2 | 11/2004 |
| WO | WO-2005000194 A2 | 1/2005 |
| WO | WO-2005/111077 A2 | 11/2005 |
| WO | WO-2006/110883 A2 | 10/2006 |
| WO | WO-2008059877 A1 | 5/2008 |
| WO | WO-2010008001 A1 | 1/2010 |
| WO | WO 2010035725 A1 * | 4/2010 |

OTHER PUBLICATIONS

Binkley, J., et al., "RNA ligands to human nerve growth factor," Nucleic Acids Research, vol. 23, No. 16, pp. 3198-3205, (1995).
Stoltenburg, R., et al., "SELEX-a (r)evolutionary method to generate high-affinity nucleic acid ligands," Biomol. Eng., vol. 24, No. 4, pp. 381-403, (2007).
Osborne, S.E., et al., "Nucleic Acid Selection and the Challenge of Combinatorial Chemistry," Chem. Rev., vol. 97, No. 2, pp. 349-370, (1997).
Cotten, M., et al., "2'-O-methyl, 2'-O-ethyl oligoribonucleotides and phosphorothioate oligodeoxyribonucleotides as inhibitors of the in vitro U7 snRNP-dependent mRNA processing event," Nucleic Acids Research, vol. 19, No. 10, pp. 2629-2635, (1991).
Ellington, A.D., et al,, "In vitro selection of RNA molecules that bind specific ligands," Nature, vol. 346, pp. 818-823, (1990).
Fitzwater, T., et al., "A SELEX Primer," Methods in Enzymology, vol. 267, pp. 275-301, (1996).
Hermann, T., et al., "Adaptive Recognition by Nucleic Acid Aptamers," Science, Vol, 287, pp. 820-825, (2000).
Hobbs, J., et al., "Polynucleotides Containing 2'-Azido-2'-deoxyribose and 2'-Azido-2'-deoxyribose," Biochemistry, vol. 12, No. 25, pp. 5138-5145, (1973).
Miyakawa, S., et al., "Aptamer Iyaku," Protein, Nucleic Acid and Enzyme, vol. 51, No. 16, pp. 2521-2527, (2006).
Lee, J.F., et al., "Aptamer therapeutics advance," Current Opinion in Chemical Biology, vol. 10, pp. 282-289, (2006).
Proske, D., et al., "Aptamers—basic research, drug development, and clinical applications," Appl. Microbiol. Biotechnol., vol. 69, pp. 367-374, (2005).
Sproat, B.S., et al., "New synthetic routes to synthons suitable for 2'-O-allyloligoribonucleotide assembly," Nucleic Acids Research, vol. 19, No. 4, pp. 733-738, (1991).
Tuerk, C., et al., "Systematic Evolution of Ligands by Exponential Enrichment: RNA Ligands to Bacteriophage T4 DNA Polymerase," Science, vol. 249, pp. 505-510, (1990).
Ulrich, H., "RNA Aptamers: From Basic Science Towards Therapy," HEP, vol. 173, pp. 305-326,(2006).
Zuker, M., "Mfold web server for nucleic acid folding and hybridization prediction," Nucleic Acids Research, vol. 31, No. 13, pp. 3406-3415, (2003).
Extended European Search Report dated Feb. 16, 2012, issued in corresponding European Application No. 09816140.9 to copending U.S. Appl. No. 13/120,650.
English Language International Search Report mailed Dec. 22, 2009, issued in International Appl. No. PCT/JP2009/066457 of which copending U.S. Appl. No. 13/120,650 is the National Stage of.

* cited by examiner

*Primary Examiner* — Dana Shin
(74) *Attorney, Agent, or Firm* — Birch, Stewart, Kolasch & Birch, LLP

(57) ABSTRACT

Provided is a higher quality aptamer having a binding activity to NGF.
An aptamer binding to NGF, which satisfies the following (1) and (2):
(1) containing the sequence represented by UGAAARAAACC (SEQ ID NO: 64) or CGAAMRAAACU (SEQ ID NO: 65), and
(2) having a base length of not more than 73.

16 Claims, 1 Drawing Sheet

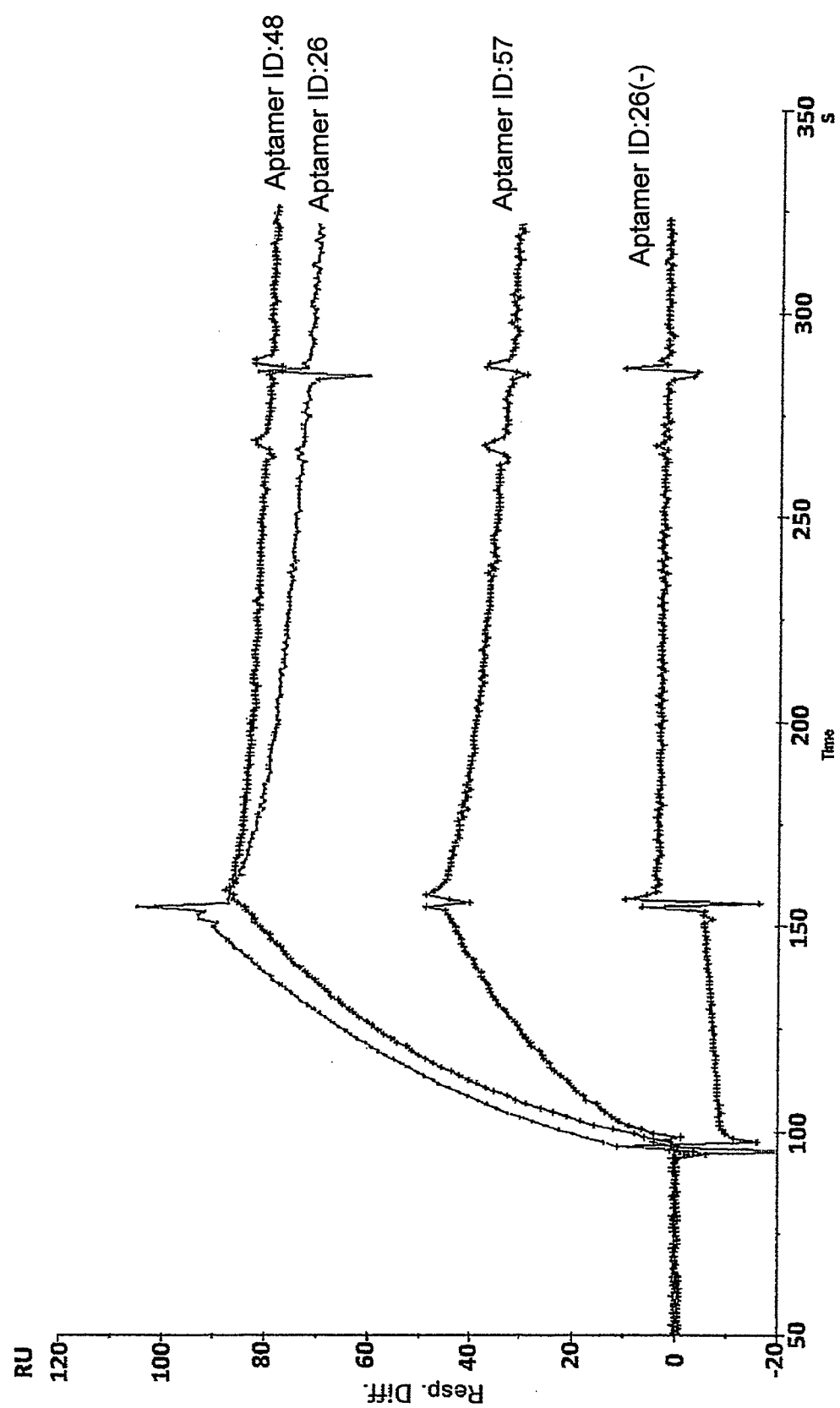

US 9,175,292 B2

APTAMER FOR NGF AND USE THEREOF

This application is the National Stage under 35 USC §371 of International Application PCT/JP2011/057105 filed on Mar. 24, 2011, which claims priority under 35 USC §119(a)-(d) of Application No. 2010-068546 filed in Japan on Mar. 24, 2010.

TECHNICAL FIELD

The present invention relates to an aptamer for NGF, a method of utilizing the same, and the like.

BACKGROUND ART

Nerve growth factor (NGF) is the first neurotrophin identified in 1951, and is an important secretory protein involved in the development and survival of peripheral and central neurons. It consists of 118 amino acids, has a molecular weight of 13 kDa, and has S—S bonds at 3 positions in a molecule. BDNF, NT-3 and NT-4/5 are present in the family protein, which are structurally well conserved and form a homodimer by a noncovalent bond. It has a β sheet structure facing 3 different directions, and is considered to be dimerized in this part. It also has four loop structures with low homology among families, and these parts are considered to define specificity to receptors.

As NGF receptors, tyrosine kinase-type receptor TrkA with high affinity and p75 with low affinity which belongs to a tumor necrosis factor receptor superfamily are known. These receptors act as a homodimer or heterodimer and are deeply involved in the development and maintenance of the nervous system. TrkA is a single-pass transmembrane receptor and has a tyrosine kinase structure in the intracellular domain. When NGF is bound, tyrosine phosphorylation occurs, the signal is transmitted to the downstream, and promotion of differentiation and survival maintenance of the cell occur.

As family receptors of TrkA, TrkB and TrkC are known. TrkB is bound to BDNF and NT-4/5, and TrkC is bound to NT-3. p75 shows lower ligand specificity as compared to TrkA and is also bound to BDNF, NT-3 and NT-4/5 besides NGF. While p75 is a single-pass transmembrane receptor, it does not have a tyrosine kinase domain on the cytoplasmic side. Like TrkA, it is expressed not only in nerve cells but also in non-nerve cells. This receptor is known to be involved in the promotion of differentiation and survival maintenance of the cell, as well as related to the induction of apoptosis and cell migration. The results of crystal structure analysis have suggested that an NGF homodimer binds to TrkA at 2:2 and to p75 at 2:1. An NGF homodimer sometimes binds to a heterodimer of TrkA and p75.

NGF is produced by Schwann cell, keratinized cell, bronchial epithelial cell, fibroblast, T lymphocyte, macrophage, mast cell, B lymphocyte, keratinocyte, smooth muscle cell, renal glomerular cell, skeletal muscle cell and the like. On the other hand, TrkA is known to be expressed in nerve cell, as well as monocyte, T lymphocyte, B lymphocyte and mast cell other than nerve cell. Similarly, p75 is expressed in nerve cell as well as non-nerve cells.

It is well known that NGF plays a key role in the nervous system. It has been clarified that NGF has an action to maintain survival of cholinergic neuron and is considered to be related in some way to Alzheimer's disease. In addition, since intracerebral administration of NGF improves memory disorders of old rats, it is also expected as a therapeutic drug for senile dementia.

It has been found that NGF also acts on the tissues and cells other than the nervous system, and involved in the body's defense and tissue repair process. For example, it is known that administration of NGF to an animal increases blood vessel permeability, enhances immune responses of T cell and B cell, induces differentiation of lymphocytes, induces growth of mast cells, induces release of various cytokines from mast cells and the like.

NGF is related to inflammation, and increased expression of NGF has been observed in patients with inflammatory diseases and inflammatory animal models. Systemic lupus erythematosus, multiple sclerosis, psoriasis, arthritis, interstitial cystitis, asthma and the like are the examples thereof. It has been reported that the synovial fluid of patients with rheumatoid arthritis shows higher NGF concentration. In addition, increased NGF expression in rheumatoid arthritis model rats, and increase in mast cells and increased NGF expression in arthritis model mouse have been reported.

NGF is deeply involved in pain. When NGF is subcutaneously administered to human, a deep pain such as muscular pain continues for several days, and hyperalgesia of the injection site occurs. NGF knockout mouse and TrkA knockout mouse lacks unmyelinated nerve and do not feel pain. When NGF is intraperitoneally administered at 1 mg/kg to a mature rat, hyperalgesia against noxious heat and mechanical stimuli occurs. NGF transgenic mouse shows hyperalgesia unaccompanied by inflammatory conditions. In addition, it is known that the TrkA gene of patients with congenital insensitivity to pain with anhidrosis (CIPA) has abnormality, and pain sensation decreases when NGF gene has abnormality.

From the above, an NGF inhibitor can be used as a therapeutic drug for pain such as nociceptive pain, inflammatory pain, neuropathic pain, carcinomatous pain, fibromyalgia pain and the like. A combination therapy of NGF antibody and NSAID (Patent reference 1), a combination therapy of NGF antibody and opioid analgesic (Patent reference 2), a treatment method of postsurgical pain using an NGF antibody (Patent reference 3, Patent reference 4), a treatment method of pain of bone cancer using an NGF antibody (Patent reference 5), and a treatment method of pain of osteoarthritis using an NGF antibody (Patent reference 6) have been reported.

Tanezumab (PF-4383119 or RN624) is an antibody against NGF, shows effect in pain model experiment using an osteoarthritis animal model, and is currently under clinical trial. While the presence or absence of inhibitory activity of NGF and NGF receptor is unknown, there is a report relating to natural RNA that binds to NGF (non-patent document 1).

In recent years, applications of RNA aptamers to medicaments, diagnostic agents, and test drugs have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target molecule such as a protein, and can be prepared using the SELEX (Systematic Evolution of Ligands by Exponential Enrichment) method (Patent references 7-9). In the SELEX, an RNA that binds specifically to a target molecule is selected from an RNA pool with about $10^{14}$ different nucleotide sequences. The RNA structure used has a random sequence of about 40 residues, which is flanked by primer sequences. This RNA pool is allowed to be assembled with a target substance, and only the RNA that has bound to the target substance is collected using a filter and the like. The RNA collected is amplified by RT-PCR, and this is used as a template for the next round. By repeating this operation about 10 times, an RNA aptamer that binds specifically to the target substance can be acquired.

Aptamer drugs, like antibody drugs, can target extracellular factors. With reference to many scientific papers and other reference materials in the public domain, aptamer drugs are judged to potentially surpass antibody drugs in some aspects. For example, aptamers often show higher binding force and higher specificity than do antibodies. Aptamers are unlikely to undergo immune elimination, and adverse reactions characteristic of antibodies, such as antibody-dependent cell-mediated cytotoxicity (ADCC) and complement-dependent cytotoxicity (CDC), are unlikely to occur with the use of aptamers. From the aspect of delivery, since aptamers are about 1/10 of antibody in size, delivery of a drug to the object site is easier. Since aptamers are produced by chemical synthesis, various modifications can be made easily, reduction of cost by large-scale production is possible. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

The present inventors have produced, in PCT/JP09/066, 457, an aptamer which binds to NGF and inhibits binding of NGF and an NGF receptor, and found that the aptamer inhibits a neurite outgrowth activity of NGF. Patent document 10 describes an aptamer to NGF, which is obtained by automated SELEX, and patent document 11 describes an altered product and a modified product of the aptamer obtained in patent document 10.

DOCUMENT LIST

Patent Documents patent document 1: WO04/073653
patent document 2: WO04/096122
patent document 3: WO04/032870
patent document 4: WO05/000194
patent document 5: WO05/111077
patent document 6: WO06/110883
patent document 7: WO91/19813
patent document 8: WO94/08050
patent document 9: WO95/07364
patent document 10: WO02/077262
patent document 11: WO03/070984

Non-Patent Document non-patent document 1: Binkley J et al., (1995) Nucleic Acids Res, 23, 3198-3205

SUMMARY OF THE INVENTION

Problems to be Solved by the Invention

The present invention aims to provide an aptamer for NGF, a method of utilizing the same, and the like. Particularly, the present invention aims to provide an aptamer having a short chain length, which is suitable for use as a pharmaceutical product.

Means of Solving the Problems

The present inventors investigated diligently to solve the problem described above and succeeded in preparing an aptamer of better quality for NGF, which resulted in the completion of the present invention.

Accordingly, the present invention provides the following.
[1] An aptamer binding to NGF, which satisfies the following (1) and (2):
(1) comprising the sequence represented by UGAAARAAACC (SEQ ID NO: 64) or CGAAM-RAAACU (SEQ ID NO: 65), and
(2) having a base length of not more than 73.
[2] The aptamer according to [1], which inhibits binding of NGF and an NGF receptor.
[3] The aptamer according to [1] or [2], which inhibits neurite outgrowth activity or cell proliferation activity of NGF.
[4] The aptamer according to [3], which has a 50% inhibitory concentration of not more than 10 nM.
[5] The aptamer according to any one of [1] to [4], which does not bind to NT-3.
[6] The aptamer according to any one of [1] to [5], which does not inhibit cell proliferation activity of BDNF, NT-3 or NT-4/5.
[7] The aptamer according to [1] or [2], comprising any one of the nucleotide sequences (a), (b) and (c) below:
(a) a nucleotide sequence selected from among SEQ ID NOs: 1-54 (wherein uracil may be thymine);
(b) a nucleotide sequence selected from among SEQ ID NOs: 1-54 (wherein uracil may be thymine), wherein 1 to several nucleotides are substituted, deleted, inserted or added; and
(c) a nucleotide sequence having an identity of 70% or more to a nucleotide sequence selected from among SEQ ID NOs: 1-54 (wherein uracil may be thymine).
[8] The aptamer according to any one of [1] to [7], wherein at least one nucleotide is modified;
[9] The aptamer according to [8], which is modified with inverted dT or polyethylene glycol.
[10] The aptamer according to [9], wherein the inverted dT or polyethylene glycol is bound to the 5' terminal or 3' terminal of the aptamer.
[11] The aptamer according to any one of [8] to [10], wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group.
[12] The aptamer according to any one of [8] to [10], wherein the hydroxyl groups at the 2'-position of a ribose of respective purine nucleotides are the same or different and unreplaced or replaced by an atom or group selected from the group consisting of a hydrogen atom, a fluorine atom and a methoxy group.
[13] A nucleic acid comprising a nucleotide sequence selected from among SEQ ID NOs: 1-54 and having a base length of not more than 73.
[14] The nucleic acid according to [13], wherein at least one nucleotide is modified.
[15] The nucleic acid according to [14], which is modified with inverted dT or polyethylene glycol.
[16] The nucleic acid according to [15], wherein the inverted dT or polyethylene glycol is bound to the 5' terminal or 3'terminal of the aptamer.
[17] The nucleic acid according to any one of [14] to [16], wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group.
[18] The nucleic acid according to any one of [14] to [16], wherein the hydroxyl groups at the 2'-position of a ribose of respective purine nucleotides are the same or different and unreplaced or replaced by an atom or group selected from the group consisting of a hydrogen atom, a fluorine atom and a methoxy group.

[19] A hydrophobic substance-added aptamer, which binds to NGF.

[20] The aptamer according to [19], which inhibits binding of NGF and an NGF receptor.

[21] The aptamer according to [20], which inhibits neurite outgrowth activity or cell proliferation activity of NGF.

[22] The aptamer according to [21], which has a 50% inhibitory concentration of not more than 10 nM.

[23] The aptamer according to [19] or [20], comprising any one of the nucleotide sequences (a'), (b') and (c') below:

(a') a nucleotide sequence selected from among SEQ ID NO: 55-63 (wherein the uracil may be thymine);

(b') a nucleotide sequence selected from among SEQ ID NO: 55-63 (wherein the uracil may be thymine), wherein 1 to several nucleotides are substituted, deleted, inserted or added; and (c') a nucleotide sequence having an identity of 70% or more to a nucleotide sequence selected from among SEQ ID NO: 55-63 (wherein the uracil may be thymine).

[24] The aptamer according to any one of [19] to [23], wherein the hydrophobic substance is bound to the 5' terminal of the aptamer.

[25] The aptamer according to any one of [19] to [24], wherein the hydrophobic substance is cholesterol.

[26] The aptamer according to any one of [19] to [25], wherein at least one nucleotide is modified.

[27] The aptamer according to [26], which is modified with inverted dT.

[28] The aptamer according to [27], wherein the inverted dT is bound to the 3' terminal of the aptamer.

[19] The aptamer according to any one of [26] to [28], wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group.

[30] The aptamer according to any one of [26] to [28], wherein the hydroxyl groups at the 2'-position of a ribose of respective purine nucleotides are the same or different and unreplaced or replaced by an atom or group selected from the group consisting of a hydrogen atom, a fluorine atom and a methoxy group.

[31] A complex comprising the aptamer according to any one of [1] to [12], [19] to [30] or the nucleic acid according to any one of [13] to [18], and a functional substance.

[32] The complex according to [31], wherein the functional substance is an affinity substance, a labeling substance, an enzyme, a drug delivery vehicle or a drug.

[33] A pharmaceutical composition comprising the aptamer according to any one of [1] to [12] and [19] to [30], the nucleic acid according to any one of [13] to [18] or the complex of [31] or [32].

[34] An anti-pain agent comprising the aptamer according to any one of [1] to [12] and [19] to [30], the nucleic acid according to any one of [13] to [18] or the complex of [31] or [32].

[35] An anti-inflammatory agent comprising the aptamer according to any one of [1] to [12] and [19] to [30], the nucleic acid according to any one of [13] to [18] or the complex of [31] or [32].

[36] A method of treating or preventing a disease accompanying a pain or inflammation, comprising administering the aptamer according to any one of [1] to [12] and [19] to [30], the nucleic acid according to any one of [13] to [18] or the complex of [31] or [32] to a subject in need thereof.

[37] The aptamer according to any one of [1] to [12] and [19] to [30], the nucleic acid according to any one of [13] to [18] or the complex of [31] or [32] for the prophylaxis or treatment of a disease accompanying a pain or inflammation.

Effect of the Invention

The aptamer of the present invention, a hydrophobic substance-added aptamer and a complex thereof can be useful as medicaments, diagnostic agents or reagents for diseases such as pain, inflammatory disease and the like. The aptamer and the complex of the present invention can also be useful for the purification and concentration of NGF, as well as detection and quantification of NGF.

BRIEF DESCRIPTION OF THE DRAWINGS

FIG. 1 is a sensorgram showing that the aptamers (Apt) shown by aptamer ID NOs: 26, 48 and 57 bind to human NGF. Aptamer ID: 26(−) means an aptamer obtained by introducing one mutation into the aptamer shown by aptamer ID: 26 (g19→g(M)), and eliminating the binding activity.

DESCRIPTION OF EMBODIMENTS

The present invention provides an aptamer binding to NGF, which comprises the sequence represented by UGAAARAAACC (SEQ ID NO: 64) or CGAAMRAAACU (SEQ ID NO: 65), and has a base length of not more than 73 (hereinafter to be described as "the aptamer of the present invention").

These sequences may have the below-mentioned modification.

The present invention provides an aptamer having a binding activity to NGF. According to preferable embodiment, the aptamer of the present invention binds to NGF, and can inhibit the activity of NGF by inhibiting the binding of NGF and an NGF receptor.

An aptamer refers to a nucleic acid molecule having a binding activity for a particular target molecule. The aptamer can inhibit the activity of a particular target molecule by binding to the particular target molecule. The aptamer of the present invention may be a nucleic acid such as an RNA, a DNA, a modified nucleic acid or a mixture thereof. The aptamer of the present invention can also be a nucleic acid in a linear or circular form.

In other words, the aptamer of the present invention may be indicated as "the nucleic acid of the present invention" in the following.

In the present Description, a sequence specified by "SEQ ID NO" means each aptamer or a nucleotide sequence of a nucleic acid and, for example, "a nucleic acid comprising the sequence shown by SEQ ID NO: 1" means a natural nucleic acid or modified nucleic acid comprising the sequence shown by SEQ ID NO: 1 or a nucleic acid constituted with the both. The base sequence of SEQ ID NO of each aptamer is described in the Sequence Listing.

NGF is a known neurotrophin, and is an important secretory protein involved in the development and survival of peripheral and central neurons. In the present invention, NGF particularly means a β type NGF. The amino acid sequences of human β-NGF are those shown by Accession Numbers NP002497, P01138, AAI26151, AAI26149 and CAB75625, which may also be one with mutation, its domain or peptide. It may be not only a monomer but also a dimer or multimer.

The aptamer of the present invention binds to NGF in a physiological buffer (e.g., solution A: see Example 2). The aptamer of the present invention binds to, for example, NGF at an intensity detectable by the following test.

For the measurement, BIAcore2000 manufactured by BIAcore is used. An aptamer is immobilized on a sensorchip. The amount to be immobilized is set to 1000 RU. A physiological buffer containing 0.3M NaCl (solution A: see Example 2) is used to prepare NGF solution (0.5 μM). This NGF solution (20 μL) is injected and the binding of NGF to the aptamer is detected. Using RNA containing a random nucleotide consisting of 40 nucleotides as a negative control, when NGF significantly strongly binds to the aptamer as compared to the control RNA, the aptamer is evaluated to have bindability to NGF.

The aptamer of the present invention inhibits the activity of NGF by binding to NGF and inhibiting the binding of NGF and an NGF receptor. In the present specification, the "inhibitory activity against NGF" means an inhibitory ability on any activity NGF has. For example, it means an activity to inhibit NGF from binding to an NGF receptor.

In addition, examples of other "inhibitory activity against NGF" include inhibition of signal transduction in the downstream of NGF receptor (Ras-MAP kinase pathway, PI3 kinase pathway), inhibition of increased expression of TRPV1, SP, BDNF and the like, inhibitory activity of expression of HA, BK, PG, NGF and other cytokine released from mast cells etc. and the like, which result from the binding of NGF to NGF receptor.

Furthermore, inhibition of differentiation, survival, neurite outgrowth of nerve cell induced by NGF, blood vessel permeability, enhancement of immune response of T cells and B cells, differentiation of lymphocytes, growth and the like of various cells such as mast cells, erythroleukemic cells, cancer cells and the like, relief of pain, hyperalgesia and the like can be mentioned.

Preferable "inhibitory activity against NGF" that the aptamer of the present invention has is an activity to inhibit the binding of NGF to NGF receptor, an activity to inhibit neurite outgrowth activity induced by NGF, an activity to inhibit cell proliferation activity induced by NGF and the like.

In the present specification, the "NGF receptor" means a cell surface protein to which NGF binds. As the NGF receptor, TrkA and p75 are known. The NGF receptor referred to in the present invention may be a protein containing a natural amino acid sequence or a variant thereof. Here, the "variant thereof" means a protein or peptide wherein several amino acids of an amino acid sequence of "NGF receptor" have been substituted or a partial amino acid sequence thereof, which has a binding activity to NGF and inhibits the binding of NGF and an NGF receptor.

The aptamer of the present invention binds to NGF and inhibits the binding of NGF and an NGF receptor. Whether or not the aptamer inhibits the binding of NGF to an NGF receptor, for example, can be evaluated by the following test.

For the measurement, BIAcore2000 manufactured by BIAcore is used. On a CM5 sensorchip is immobilized a fusion protein of NGF receptor and Fc (e.g., Trk A-Fc (175-TK, R&D systems)) or p75-Fc (R&D systems)). The amount to be immobilized is 500 to 700 RU. NGF (0.1 μM) and an aptamer (0.2 μM) are mixed in a physiological buffer (solution A: see below-mentioned Example 2), and a mixture to be a sample is prepared over 30 min. This mixture is injected into BIAcore2000, and the binding of NGF to an NGF receptor is detected.

When the inhibitory activity (%) is not less than 90%, the aptamer is evaluated to inhibit the binding of NGF to NGF receptor. The inhibitory activity (%) is calculated with the binding amount of NGF and NGF receptor, excluding aptamer, as 0, and a binding amount by injection of an NGF-free solution as 100. Here, the binding amount means RU value at a peak top of the sensorgram of BIAcore (RU value immediately after completion of NGF injection).

In one embodiment, the aptamer of the present invention can inhibit both the binding of NGF and TrkA, and that of NGF and p75.

The aptamer of the present invention can exhibit inhibitory activity against NGF derived from any mammals. Such mammals include primates (e.g., human, monkey), rodents (e.g., mouse, rat and guinea pig), and companion animals, domestic animals and working animals (e.g., dog, cat, horse, bovine, goat, sheep, swine).

The aptamer of the present invention is not particularly limited as long as it binds to any portion of NGF and can inhibit the binding of NGF to an NGF receptor.

The aptamer of the present invention comprises the sequence represented by UGAAARAAACC (SEQ ID NO: 64) or CGAAMRAAACU (SEQ ID NO: 65). M in SEQ ID NO: 65 means adenosine or cytidine, and R in SEQ ID NOs: 64 and 65 means guanosine or adenosine. As the sequence shown by SEQ ID NO: 64, UGAAAAAAACC (SEQ ID NO: 66) or UGAAAGAAACC (SEQ ID NO: 67) can be recited as an example. As the sequence shown by SEQ ID NO: 65, CGAACAAAACU (SEQ ID NO: 68) or CGAAAGAAACU (SEQ ID NO: 69) can be recited as an example.

These sequences may have the below-mentioned modification.

Also, the aptamer of the present invention characteristically has a base length of not more than 73.

Since an aptamer of 74 nucleotides or above has a long chain length, it is often difficult to be applied to use as a pharmaceutical product. In other words, when the total number of nucleotides is smaller than 73, chemical synthesis and mass-production of the aptamer will be easier, and there is a major advantage in terms of cost. It is also thought that chemical modification is easier, stability in the body is higher, and toxicity is lower.

From the viewpoint of application to a pharmaceutical product use, the aptamer of the present invention more desirably has a base length shorter than 73 nucleotides, preferably not more than 70 nucleotides, still more preferably not more than 50 nucleotides, most preferably not more than 45 nucleotides. On the other hand, when the total number of nucleotides of the "nucleic acid" region is too small, the aptamer may not be able to bind to NGF to inhibit the binding of NGF to an NGF receptor. An appropriate minimum number of nucleotides can be appropriately determined by those of ordinary skill in the art according to the object.

In addition, the aptamer of the present invention can be an aptamer that binds to NGF, and/or inhibits the binding of NGF to an NGF receptor, thereby inhibiting a neurite outgrowth activity or cell proliferation activity of NGF. Whether the aptamer of the present invention can inhibit neurite outgrowth activity of NGF can be evaluated by the test described in Example 3. In addition, whether the aptamer of the present invention can inhibit cell proliferation activity of NGF can be evaluated by the test described in Example 4.

The concentration of the aptamer of the present invention at which the neurite outgrowth activity of NGF or cell proliferation activity of NGF is 50% (IC50; 50% inhibitory concentration) is preferably not more than 10 nM, more preferably not more than 1 nM.

Each nucleotide contained in the aptamer of the present invention is the same or different and can be a nucleotide comprising a hydroxyl group at the 2'-position of ribose (e.g., ribose of pyrimidine nucleotide, ribose of purine nucleotide) (i.e., unsubstituted nucleotide) or a nucleotide wherein a hydroxyl group is replaced by any atom or group at the 2'-position of ribose. As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH₂ group) can be mentioned. In the following cases, the hydroxyl group is replaced by a hydrogen atom, a fluorine atom or —O-Me group, respectively, at the 2'-position of ribose.

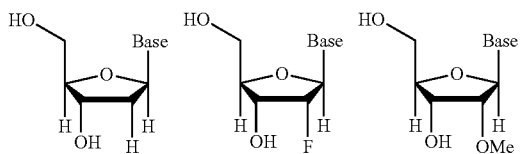

The aptamer of the present invention can also be the nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2'-position of ribose.

Also, in the aptamer of the present invention, all pyrimidine nucleotides are the same or different and each can be a nucleotide substituted by a fluorine atom, or a nucleotide substituted by any atom or group mentioned above, preferably an atom or group selected from the group consisting of a hydrogen atom, a hydroxyl group and a methoxy group at the 2'-position of ribose.

In the aptamers of the present invention, moreover, all purine nucleotides are the same or different and each can be a nucleotide substituted by a hydroxyl group, or a nucleotide substituted by any atom or group mentioned above, preferably an atom or a group selected from the group consisting of a hydrogen atom, a methoxy group, and a fluorine atom at the 2'-position of ribose.

In the aptamers of the present invention, moreover, all nucleotides comprise a hydroxyl group, or any atom or group mentioned above, for example, the identical group selected by the group consisting of a hydrogen atom, a fluorine atom, a hydroxyl group and a —O-Me group at the 2'-position of ribose.

In this specification, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, replacement of the hydroxyl group at the 2'-position of ribose by X should read as a replacement of one hydrogen atom at the 2'-position of deoxyribose by X.

When uracil is substituted with thymine in the aptamer of the present invention, NGF-binding activity, NGF-NGF receptor binding inhibitory activity, NGF neurite outgrowth inhibitory activity, NGF cell proliferation inhibitory activity, stability, drug deliverability and stability in blood of the aptamer and the like can be increased.

Alternatively, the aptamer of the present invention is characteristically free of binding activity to neurotrophin 3 (hereinafter to be indicated as NT-3). Here, being free of binding activity to NT-3 mean that binding of each protein and the aptamer of the present invention is below detection limit in various binding assays. Specifically, it means, for example, that a response cannot be obtained in a surface plasmon resonance sensorgram, which can be measured by the method described in Example 7.

Alternatively, the aptamer of the present invention characteristically does not inhibit cell proliferation activity of neurotrophin other than NGF, specifically, brain-derived neurotrophic factor (hereinafter to be indicated as BDNF), NT-3 and neurotrophin 4/5 (hereinafter to be indicated as NT-4/5). Here, whether the aptamer inhibits cell proliferation activity of other neurotrophins (BDNF, NT-3, NT-4/5) can be evaluated by the test described in Example 7. That the cell proliferation activity of BDNF, NT-3 or NT-4/5 is not inhibited means, for example, that the concentration of the aptamer of the present invention necessary for inhibiting cell proliferation of each neurotrophin by 50% (IC50; 50% inhibitory concentration) is not less than 100 nM, preferably not less than 300 nM, more preferably not less than 1000 nM, for BDNF and NT-3, and not less than 100 nM, preferably not less than 300 nM, for NT-4/5.

A more preferable embodiment of the aptamer of the present invention is an aptamer that does not inhibit cell proliferation activity of BDNF, NT-3 and NT-4/5.

In the present specification, the terms BDNF, NT-3 and NT-4/5 mean BDNF, NT-3 and NT-4/5 of all mammalian species including human, respectively.

The aptamer of the present invention can also be:
(a) an aptamer comprising a nucleotide sequence selected from among SEQ ID NOs:1-54 (wherein the uracil may be thymine);
(b) an aptamer comprising a nucleotide sequence selected from among SEQ ID NOs:1-54 (wherein the uracil may be thymine), wherein one to several nucleotides are substituted, deleted, inserted or added;
(c) an aptamer comprising a nucleotide sequence having an identity of 70% or more (preferably 80% or more, more preferably 90% or more, most preferably 95% or more) to a nucleotide sequence selected from among SEQ ID NOs: 1-54 (wherein the uracil may be thymine); or
(d) a conjugate selected from the group consisting of a conjugate of a plurality of aptamers (a) above, a conjugate of a plurality of aptamers (b) above, a conjugate of a plurality of aptamers (c) above, and a conjugate of a plurality of aptamers (a), (b) and (c) above.

The aptamers of the above-mentioned (b)-(d) can bind to NGF and/or inhibit the activity of NGF (NGF receptor binding activity etc.).

In addition, preferably, the aptamers of the above-mentioned (b)-(d) bind to NGF and inhibit the binding of NGF and an NGF receptor, and/or bind to NGF, and inhibit the neurite outgrowth activity or cell proliferation activity of NGF.

More preferably, the aptamers of the above-mentioned (b)-(d) show an NGF neurite outgrowth or cell proliferation activity inhibitory concentration of not more than 10 nM, more preferably not more than 1 nM.

In (b) above, the number of nucleotides substituted, deleted, inserted or added is not particularly limited as long as the aptamer binds to NGF, and can inhibit the activity of NGF (NGF receptor binding activity etc.) and as long as the nucleotide number of the aptamer itself does not exceed 73. It can be, for example, not more than about 30, preferably not more than about 20, more preferably not more than about 10, still more preferably not more than 5, most preferably 4, 3, 2 or 1.

With respect to (c) above, "an identity" means a ratio (%) of identical nucleotide residues to all overlapping nucleotide residues in the optimal alignment where two nucleotide sequences are aligned using a mathematical algorithm known in the technical field (preferably, the algorithm considers introduction of gaps on one or both of the sequences for the best alignment).

Nucleotide sequence identity can be calculated by, for example, aligning the two nucleotide sequences using the homology calculation algorithm NCBI BLAST-2 (National Center for Biotechnology Information Basic Local Alignment Search Tool) under the following conditions (gap open=5 penalties; gap extension=2 penalties; x_ dropoff=50; expectation value=10; filtering=ON).

In (d) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4. Each of the nucleotides in (a) to (d) above, whether the same or different, can be a nucleotide comprising a hydroxyl group at the 2'-position of ribose (e.g., ribose of pyrimidine nucleotide), or a nucleotide wherein a hydroxyl group is replaced by any groups (e.g., a hydrogen atom, fluorine atom or —O-Me group) at the 2'-position of ribose.

The aptamer of the present invention may be one wherein a sugar residue (e.g., ribose) of each nucleotide has been modified to increase the NGF-binding activity, NGF-NGF receptor binding inhibitory activity, NGF neurite outgrowth inhibitory activity, NGF cell proliferation inhibitory activity, stability, drug deliverability, and stability in blood of the aptamer and the like. Examples of the modification in a sugar residue include replacement of oxygen atom at the 2'-position, 3'-position and/or 4'-position of the sugar residue with another atom, and the like. As the kind of the modification, fluorination, O-alkylation (e.g., O-methylation, O-ethylation), O-arylation, S-alkylation (e.g., S-methylation, S-ethylation), S-arylation, and amination (e.g., —NH$_2$) can be mentioned. In addition, examples thereof include 4'-SRNA wherein the 4'-position oxygen is replaced with sulfur, LNA wherein the 2'-position and the 4'-position are crosslinked via methylene (Locked Nucleic Acid), 3'-N-phosphoramidate nucleic acid wherein the 3'-position hydroxyl group is replaced with an amino group and the like. Such alterations in the sugar residue can be performed by a method known per se (see, for example, Sproat et al., (1991) Nucl. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the NGF-binding activity, NGF-NGF receptor binding inhibitory activity, NGF neurite outgrowth inhibitory activity, NGF cell proliferation inhibitory activity, stability, drug deliverability, and stability in blood of the aptamer and the like. As examples of such alterations, pyrimidine alteration at 5-position, purine alteration at 6- and/or 8-position(s) (O-methyl modification and the like), alteration with an extracyclic amine, substitution with 4-thiouridine, and substitution with 5-bromo or 5-iodo-uracil can be mentioned. The phosphate group contained in the aptamer of the present invention may be altered to confer resistance to nuclease and hydrolysis. For example, the phosphate region of the aptamer may be replaced with P(O)S (thioate), P(S)S (dithioate), P(O)NR$_2$ (amidate), P(O)R, P(O)OR', CO or CH$_2$ (formacetal), P(O)BH$_3$ (boranophosphate) or 3'-amine (—NH—CH$_2$—CH$_2$—) [wherein each unit of R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethyleneglycol (hereinafter, sometimes to be described as "PEG"), amino acid, peptide, inverted dT, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703

Particularly, when alteration is performed by terminal addition of PEG, the molecular weight of PEG is not particularly limited, and is preferably 1000-100000, more preferably 30000-90000. PEG may be linear or branched into two or more chains (multi-arm PEG).

Such PEG is not particularly limited, and those of ordinary skill in the art can appropriately select and use commercially available or known PEG. Specific preferable examples of the PEG to be applied to the aptamer of the present invention include 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION) and the like.

In this case, in the aptamer of the present invention, PEG may be directly added to the terminal. It is more preferable that a linker having a group bindable to PEG and the like be added to the terminal thereof, and PEG be added to the aptamer of the present invention via the linker.

The linker for PEG and the aptamer of the present invention is not particularly limited, and carbon chain number, functional group and the like can be appropriately selected according to the binding site, the kind of PEG and the like. Examples of such linker include a linker having an amino group. Specifically, when added to the 5' terminal, ssH Linker (SAFC) or DMS (O)MT-AMINO-MODIFIER (GLENRESERCH) can be mentioned, and when added to the 3' terminal, TFA Amino C-6 lcaa CPG (ChemGenes) and the like can be mentioned. When this linker is selected, for example, an active group of N-hydroxysuccinimide is added to PEG, and reacted with an amino group on the linker side, whereby the aptamer of the present invention can be bound to PEG via the linker.

As PEG and linker, commercially available products can be preferably used. The reaction conditions and the like relating to the binding of PEG, a linker and the aptamer of the present invention can be appropriately determined by those of ordinary skill in the art.

The aptamer of the present invention can be chemically synthesized as disclosed herein and by a method known per se in the art. An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to the positive charge of lysine and arginine present on the surface of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to an active site of the target substance. Therefore, the aptamers obtained by SELEX do not necessarily act on the function of the target substance. NGF is a basic protein, and is thought to be likely to allow nucleic acids to bind thereto nonspecifically. An aptamer that does not bind to an active site does not influence the activity of the target substance. In fact, the RNA used for control did not inhibit the binding of NGF and an NGF receptor.

Based on an active aptamer thus selected, SELEX can be performed based on the sequence of the obtained aptamer to acquire an aptamer possessing higher activity. Specifically, after preparing a template wherein an aptamer with a determined sequence is partially randomized or a template doped with about 10 to 30% of random sequences, SELEX is performed again.

An aptamer obtained by SELEX has a length of about 80 nucleotides, and this is difficult to prepare as a medicament as it is. Hence, it is necessary to repeat try-and-error efforts to shorten the aptamer to a length of 73 nucleotides or less enabling easy chemical synthesis, preferably 70 nucleotides or less, more preferably 60 nucleotides or less, further preferably 50 nucleotides or less, most preferably 45 nucleotides or less. Depending on the primer design for an aptamer obtained by SELEX, the ease of the subsequent minimization operation changes. Unless the primer is designed successfully, subsequent development will be impossible even if an aptamer with activity is selected by SELEX. In the present invention, an aptamer retaining activity even with 43 nucleotides was obtained.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the obtained aptamer with the target substance is identified by repeated try-and-error efforts as described above, the activity remains unchanged in many cases even when a new sequence is added to both ends of the sequence. Such length of the new sequence is not particularly limited.

Particularly, the aforementioned sequences shown by UGAAARAAACC (SEQ ID NO: 64) and CGAAM-RAAACU (SEQ ID NO: 65) are important portions for binding of the aptamer of the present invention to NGF and inhibition of the binding of NGF and an NGF receptor. Even when a new sequence is added to both ends of these sequences, the activity remains unchanged in many cases. These sequences may have the aforementioned modifications.

Modifications, like sequences, afford a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:
Primer sequence (i)-(N)a-fixed sequence-(N)b-Primer sequence (ii)
[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The aptamer of the present invention is preferably an aptamer that binds to NGF, characteristically contains the sequence shown by SEQ ID NO: 26, and has a base length of not more than 73.

The sequence shown by SEQ ID NO: 26 is a region important for the aptamer of the present invention to function as the aptamer of the present invention such as binding to NGF, inhibition of the binding of NGF to an NGF receptor and the like. Even when a new sequence is added to both ends of the sequence, the function of the aptamer of the present invention is not impaired. The sequence may be subject to modification of the aforementioned sugar residue, alteration of nucleic acid base and phosphate group, and the like.

Thus, preferable specific examples of the aptamer of the present invention include
aptamers comprising the sequence shown by SEQ ID NO: 26, having a base length of not more than 73, and binding to NGF, which are
(i) an aptamer comprising at least one kind of nucleotide wherein the hydroxyl group is replaced by a hydrogen atom, a fluorine atom, a —O-alkyl group, a —O-acyl group or an amino group at the 2'-position of ribose;
(ii) an aptamer wherein PEG, amino acid, peptide, inverted dT, myristoyl, lithocolic-oleyl, docosanyl, lauroyl, stearoyl, palmitoyl, oleoyl, linoleoyl, other lipid, steroid, cholesterol, caffeine, vitamin, dye, a fluorescent substance, an anti-cancer agent, a toxin, an enzyme, or a radioactive substance or biotin is added to the terminal;
(iii) an aptamer that satisfies the requirements of (i) and (ii); and the like.

The present invention also provides a hydrophobic substance-added aptamer binding to NGF (hereinafter to be indicated as "a hydrophobic substance-added aptamer of the present invention").

In the present specification, the hydrophobic substance-added aptamer is an aptamer bound to a hydrophobic substance. That is, the hydrophobic substance-added aptamer of the present invention is a substance wherein an "aptamer" region and a "hydrophobic substance" region are bound. The "aptamer" region and the "hydrophobic substance" region may be bound by a "linker" region.

The "aptamer" region of the hydrophobic substance-added aptamer of the present invention is as explained earlier for "the aptamer of the present invention". Therefore, the kind of the nucleotide constituting the aptamer region is not particularly limited as long as the hydrophobic substance-added aptamer binds to NGF. That is, as long as the earlier conditions are satisfied, it may be any of nucleotides known per se such as DNA, RNA and the like, modified nucleic acid and a mixture thereof, and a double strand or a single strand. In addition, the sequence of nucleotide per se is not particularly limited. Unless particularly specified, the above-mentioned "modified nucleic acid" refers to a "nucleotide substituted (modified) at a substitutable position" shown below.

Alternatively, the hydrophobic substance-added aptamer of the present invention can be a hydrophobic substance-added aptamer that binds to NGF to inhibit the binding of NGF to an NGF receptor. Whether the hydrophobic substance-added aptamer of the present invention inhibits the binding of NGF to an NGF receptor can be evaluated by the test in "the aptamer of the present invention" above or the test described in Example 2.

The hydrophobic substance-added aptamer of the present invention can be a hydrophobic substance-added aptamer that binds to NGF to inhibit neurite outgrowth activity of NGF or cell proliferation activity of NGF. Whether the hydrophobic substance-added aptamer of the present invention inhibits the neurite outgrowth activity of NGF can be evaluated by the test in "the aptamer of the present invention" above or the test described in Example 3. Whether the hydrophobic substance-added aptamer of the present invention inhibits the cell proliferation activity of NGF can be evaluated by the test in "the aptamer of the present invention" above or the test described in Example 4.

The concentration of the hydrophobic substance-added aptamer of the present invention at which the neurite outgrowth activity of NGF or cell proliferation activity of NGF is 50% (IC50; 50% inhibitory concentration) is preferably not more than 10 nM, more preferably not more than 3 nM.

The nucleotide contained in the hydrophobic substance-added aptamer of the present invention can be, like the aptamer of the present invention, a nucleotide comprising a hydroxyl group at the 2'-position of ribose (i.e., an unsubstituted nucleotide) or a nucleotide wherein a hydroxyl group is replaced by any atom or group at the 2'-position of ribose. Examples of any such atom or group include atoms and groups similar to those recited for the aptamer of the present invention.

While the base length of the "aptamer" region of the hydrophobic substance-added aptamer of the present invention is not particularly limited as long as the hydrophobic substance-added aptamer binds to NGF and inhibits the binding of NGF to an NGF receptor, it is desirably not more than 73 nucleotides (when 5' terminal or 3' terminal is modified with inverted dT, this is not counted as the base length).

Since a hydrophobic substance-added aptamer of 74 nucleotides or above has a long chain length, it is often difficult to be applied to use as a pharmaceutical product. In other words, when the total number of nucleotides is smaller than 73, chemical synthesis and mass-production of the aptamer will be easier, and there is a major advantage in terms of cost. It is also thought that chemical modification is easier, stability in the body is higher, and toxicity is lower.

From the viewpoint of application to a pharmaceutical product use, the hydrophobic substance-added aptamer of the present invention more desirably has a base length shorter than 73 nucleotides, preferably not more than 70 nucleotides, still more preferably not more than 50 nucleotides, most preferably not more than 45 nucleotides. On the other hand, when the total number of nucleotides of the "nucleic acid" region is too small, the aptamer may not be able to bind to NGF to inhibit the binding of NGF to an NGF receptor. An appropriate minimum number of nucleotides can be appropriately determined by those of ordinary skill in the art according to the object.

The nucleotide constituting the "aptamer" region may be substituted (modified) in any manner at any substitutable position, as long as the hydrophobic substance-added aptamer binds to NGF and inhibits the binding of NGF to an NGF receptor. It may a nucleotide not substituted (modified) at all. When substituted (modified), the "substitutable position" is clear to those of ordinary skill in the art and they can select a substituent known per se.

Of the nucleotides constituting the "aptamer" region, the nucleotide substituted (modified) at a substitutable position (sometimes to be indicated as a modified nucleic acid in the present specification) is preferably a nucleotide wherein the 2'-position of ribose (e.g., ribose of pyrimidine nucleotide) is a hydroxyl group (i.e., unsubstituted nucleotide), or a nucleotide wherein the hydroxyl group is replaced at the 2'-position of ribose with the same or different any atom or substituent.

Examples of the above-mentioned atom or substituent include a hydrogen atom, a halogen atom (e.g., a fluorine atom), a —O-alkyl group (e.g., —O-Me group), a —O-acyl group (e.g., —O—CHO group), an amino group (e.g., —NH$_2$ group) and the like.

In this specification, the nucleotides constituting the hydrophobic substance-added aptamer are assumed to be RNAs (i.e., the sugar groups are assumed to be ribose) in describing how the sugar groups are modified in the nucleotides. However, this does not mean that DNA is exempted from the hydrophobic substance-added aptamer-constituting nucleotides, and a modification of RNA should read as a modification of DNA as appropriate. When the nucleotide constituting the aptamer is DNA, for example, replacement of the hydroxyl group at the 2'-position of ribose by X should read as a replacement of one hydrogen atom at the 2'-position of deoxyribose by X.

When uracil is substituted with thymine in the hydrophobic substance-added aptamer of the present invention, NGF-binding activity, NGF-NGF receptor binding inhibitory activity, NGF neurite outgrowth inhibitory activity, NGF cell proliferation inhibitory activity, stability, drug deliverability and stability in blood of the aptamer and the like can be increased.

The hydrophobic substance-added aptamer of the present invention can also be:
(a) a hydrophobic substance-added aptamer comprising a nucleotide sequence selected from among SEQ ID NOs: 55-63 (wherein the uracil may be thymine);
(b) a hydrophobic substance-added aptamer comprising a nucleotide sequence selected from among SEQ ID NOs: 55-63 (wherein the uracil may be thymine), wherein one to several nucleotides are substituted, deleted, inserted or added; (c) a hydrophobic substance-added aptamer comprising a nucleotide sequence having an identity of 70% or more (preferably 80% or more, more preferably 90% or more, most preferably 95% or more) to a nucleotide sequence selected from among SEQ ID NOs: 55-63 (wherein the uracil may be thymine); or
(d) a conjugate selected from the group consisting of a conjugate of a plurality of aptamers (a') above, a conjugate of a plurality of aptamers (b') above, a conjugate of a plurality of aptamers (c') above, and a conjugate of a plurality of aptamers (a'), (b') and (c') above.

The aptamers of the above-mentioned (b')-(d') or a conjugate can bind to NGF and/or inhibit the activity of NGF (NGF receptor binding activity etc.).

In addition, preferably, the aptamers of the above-mentioned (b')-(d') or a conjugate bind to NGF and inhibit the binding of NGF and an NGF receptor, and/or bind to NGF, and inhibit the neurite outgrowth activity of NGF.

More preferably, the aptamers of the above-mentioned (b')-(d') or a conjugate show an NGF neurite outgrowth or cell proliferation activity inhibitory concentration of not more than 10 nM, more preferably not more than 3 nM.

In (b') above, the number of nucleotides substituted, deleted, inserted or added is not particularly limited as long as the aptamer binds to NGF, and can inhibit the activity of NGF (NGF receptor binding activity etc.) and the nucleotide number of the aptamer per se is not more than 73. It can be, for example, not more than about 30, preferably not more than about 20, more preferably not more than about 10, still more preferably not more than 5, most preferably 4, 3, 2 or 1.

In (d') above, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4. Each of the nucleotides in (a') to (d') above, whether the same or different, can be a nucleotide comprising a hydroxyl group at the 2'-position of ribose (e.g., ribose of pyrimidine nucleotide), or a nucleotide wherein a hydroxyl group is replaced by any groups (e.g., a hydrogen atom, a fluorine atom or —O-Me group) at the 2'-position of ribose.

The "sugar residue" region, "nucleic acid base" region and "phosphate group" region, as well as substitution (modification), alteration and the like thereof in the hydrophobic substance-added aptamer of the present invention are similar to those explained for the aptamer of the present invention.

In the hydrophobic substance-added aptamer of the present invention, an alteration can further be performed by adding to an end PEG, amino acid, peptide, inverted dT, myristoyl, lithocolic-oleyl, docosanyl, lauroyl, stearoyl, palmitoyl, oleoyl, linoleoyl, other lipids, steroids, cholesterol, caffeine, vitamins, pigments, fluorescent substances, anticancer agent, toxin, enzymes, radioactive substance, biotin and the like. The above-mentioned alteration can be handled in the same manner as in the aptamer of the present invention.

The substance constituting the "hydrophobic substance" region the hydrophobic substance-added aptamer of the present invention may be substituted (modified) in any manner at any substitutable position, as long as the hydrophobic substance-added aptamer binds to NGF and inhibits the binding of NGF to an NGF receptor. The "substitutable position" is clear to those of ordinary skill in the art and they can select a substituent known per se.

When such "hydrophobic substance" is bound to an aptamer, NGF-binding activity, NGF-NGF receptor binding inhibitory activity, NGF neurite outgrowth inhibitory activity, NGF cell proliferation inhibitory activity, stability, drug deliverability and stability in blood of the aptamer and the like can be increased.

In the present specification, as the "hydrophobic substance", the below-mentioned steroids and vitamins can be specifically mentioned, sterols can be preferably mentioned, and cholesterols can be more preferably mentioned.

In the present specification, the "steroids" means a compound having a cyclopentaphenanthrene skeleton or a skeleton resulting from one or more from cleavage of ring binding, ring expansion and ring contraction therefrom as a basic skeleton, wherein the entirety or a part thereof is hydrogenated. As steroids, strophanthidin, cholestanol, steroid hormone (testosterone, estradiol, progesterone, cortisol, cortisone, aldosterone, corticosterone, deoxycorticosterone and the like), and the like can be specifically mentioned. They may be known vitamins, specific vitamin A, vitamin D, vitamin E, vitamin K and the like.

In the present specification, the "sterols" means a compound wherein the C-3 position of ring A in the cyclopentaphenanthrene skeleton of steroids is hydroxylated or carbonylated. As sterols, steroid hormone, campesterol, sitosterol, stigmasterol, ergosterol and the like can be specifically mentioned.

In the present specification, the "cholesterols" means an animal-derived sterol, which includes not only cholesterol but also hydrogenated cholesterol and one derivatized by an ester reaction. As such cholesterol derivative, hydrogenated dihydrocholesterol, and ester with lower or higher fatty acid can be mentioned. Cholesteryl hydroxystearate, cholesteryl oleate, cholesteryl isostearate, cholesteryl lanolate, cholesteryl macadamiate, cholesteryl nonanoate, cholesteryl stearate, cholesteryl butyrate and the like are commercially available.

The hydrophobic substance-added aptamer of the present invention may have an "aptamer" region directly bound to a "hydrophobic substance" region, or an "aptamer" region bound to a "hydrophobic substance" region via a "linker"

region. Those of ordinary skill in the art can bind an "aptamer" region and a "hydrophobic substance" region by a known method.

In the hydrophobic substance-added aptamer of the present invention, the "linker" region capable of binding an "aptamer" region to a "hydrophobic substance" region is not particularly limited as long as a hydrophobic substance-added aptamer can bind to NGF and inhibit the binding of NGF to an NGF receptor, and those of ordinary skill in the art can appropriately determine such linker.

Examples of such linker include saturated hydrocarbon chain (e.g., saturated hydrocarbon chain having a carbon number of 12), nucleotide chain (e.g., 1 to about 20 nucleotides), non-nucleotide chain (e.g., $-(CH_2)_n$-linker, peptide-containing linker (e.g., -Gly-Cys-), $-S-S$-bond-containing linker (e.g., $-(CH_2)_m-S-S-(CH_2)_n-$), $-CONH$-bond-containing linker (e.g., $-(CH_2)_m-CONH-(CH_2)_n-$, $-O-CO-NH-(CH_2)_n-$), $-OPO_3$-bond-containing linker (e.g., $-(CH_2)_m-O-PO_2-O-(CH_2)_n-$), polyethylene glycol linker (e.g., hexaethyleneglycol linker)) and the like (m and n in each linker mean any integer).

The above-mentioned linker region may be branched and added with a functional molecule such as dimethoxytrityl group (DMT), fluorescent substance and the like (these functional molecules are finally removed in some cases). Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

Examples of the above-mentioned "saturated hydrocarbon chain" include those having a carbon number of 3, 6, 12, 18 or 24. it may also be branched.

As the above-mentioned "nucleotide chain", a nucleotide containing a hydroxyl group at the 2'-position of ribose (e.g., ribose of pyrimidine nucleotide), or a nucleotide wherein a hydroxyl group is replaced (modified) with any group (e.g., a hydrogen atom, a fluorine atom or $-O-Me$ group) at the 2'-position of ribose can be mentioned.

The binding the "linker" region and the "hydrophobic substance" region is not particularly limited, and the both regions can be bound by a method known to those of ordinary skill in the art.

In addition, the binding the "linker" region and the "aptamer" region is not particularly limited, either, and the both regions can be bound by a method known to those of ordinary skill in the art.

The "linker" region and the "hydrophobic substance" region of the hydrophobic substance-added aptamer of the present invention may be bound on the 5' terminal or 3' terminal side of the "aptamer" region. It may also be bound both on the 5' terminal and 3' terminal sides of the "aptamer" region. It may also be bound to a nucleic acid base or ribose or phosphate region in the sequence of the "aptamer" region.

The "aptamer" region in the hydrophobic substance-added aptamer of the present invention can be produced by a method similar to the production method of the aptamer of the present invention described earlier. The hydrophobic substance-added aptamer of the present invention can be chemically synthesized by a method known per se in the art. For example, cholesterol can be added to the 5' terminal of a synthesized aptamer by using commercially available cholesterol TEG phosphoramidite (manufactured by Glen Research). In this case, any linker can also be added between the aptamer and cholesterol by simultaneously using commercially available amidite Spacer18 (manufactured by Glen Research) and the like.

In addition, using commercially available 3'-cholesterol TEG-CPG (manufactured by Glen Research), cholesterol can be added to the 3' terminal of an aptamer. In the same manner as in the above, any linker can also be added between the aptamer and cholesterol by simultaneously using commercially available amidite Spacer18 (manufactured by Glen Research) and the like.

Using a similar method, cholesterol can also be added to a nucleic acid base or ribose or phosphate region in the sequence.

Furthermore, when an amino group is added to the terminal or in an aptamer, cholesterol can be added by a coupling reaction after synthesis of nucleic acid using a synthesizer.

For addition of an amino group to the 5' terminal of the aptamer, commercially available 5'-amino-modifier C6-TFA (manufactured by Glen Research) and the like can be used.

For addition of an amino group to the 3' terminal of the aptamer, commercially available 3'-amino-modifier C7-CPG (manufactured by Glen Research) and the like can be used.

Cholesterol can be added in the aptamer by using an amino group in nucleic acid base, or introducing an amino group into the 5-position of pyrimidine, the 6-position of purine and the like. Moreover, an amino group may be introduced into the 2'-position of ribose or phosphate region.

A coupling reaction of cholesterol and an amino group can be easily performed by adding an active group to cholesterol. As a result, the hydrophobic substance-added aptamer of the present invention can be produced.

The present invention also provides a complex comprising the aptamer of the present invention (hereinafter including hydrophobic substance-added aptamer) and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a medicament or a diagnostic agent, a test drug, a reagent, an additive for drinking water and food, an enhancer and a mitigator.

The aptamer and complex of the present invention can have an activity to inhibit the function of NGF by binding to NGF and inhibiting the binding of NGF and an NGF receptor. As mentioned above, NGF is deeply involved in the pain and inflammation. Therefore, the aptamer (hydrophobic substance-added aptamer) and complex of the present invention are useful as medicaments for the prophylaxis or treatment of diseases accompanying pain or inflammation (anti-pain agent, anti-inflammatory agent etc.).

Here, examples of the pain include nociceptive pain (muscular pain, back pain, upper limb pain, whiplash injury, arthralgia, osteoarthritis, gout, rheumatoid arthritis, headache, migraine headache, catatonic headache, cluster headache, secondary headache, orofacial pain, toothache, causalgia after tooth extraction, phantom tooth pain, organ pain, cardiac pain, abdominal pain, mittelschmerz, dysmenorrhea, labor pain, nephralgia, ureteralgia, ostalgia and the like), inflammatory pain, neuropathic pain (diabetic neuropathy, toxic neuropathy, pain after operation, phantom limb pain, fragment pain, reflex sympathetic dystrophy, causalgia, postherpetic pain, trigeminal neuralgia, central pain), carcinomatous pain (pain due to cancer infiltration into visceral organ, pain caused by blood vessel obstruction due to blood vessel infiltration of cancer tissue, pain of bone metastasis, pain associated with intracerebral metastasis, pain caused by peripheral nerve infiltration of cancer tissue), fibromyalgia pain and the like.

While the disease associated with inflammation here is not particularly limited, systemic lupus erythematosus, multiple sclerosis, psoriasis, osteoarthritis, rheumatoid arthritis, interstitial cystitis, asthma and the like can be mentioned.

While the above-mentioned cancer is not particularly limited, esophagus cancer, thyroid cancer, urinary bladder cancer, colorectal cancer, gastric cancer, pancreatic cancer, thoracic cancer, liver cancer, lung cancer, non-small cell lung cancer, breast cancer, neuroblastoma, neuroblastoma, glioblastoma, uterine cancer, cervical cancer, ovarian cancer, Wilms' tumor, prostate cancer and the like can be mentioned.

When NGF binds to a receptor thereof, TrkA, it activates tyrosine phosphorylation of TrkA and Ras-MAPK, PLC-γ, PI3K and the like at the downstream of TrkA, and exhibits physiological actions such as survival and differentiation of nerve cells. On the other hand, it induces cell death in the signal pathway via p75 receptor. Therefore, the aptamer and complex of the present invention can be used as medicaments, diagnostic agents, test drugs, or reagents for diseases relating to activation of these signal transduction pathways. Examples of the diseases relating to the activation of these signal transduction pathways include the above-mentioned pains, inflammatory disease and cancers.

When the aptamer and complex of the present invention are used as medicaments, diagnostic agents, test drugs, reagents and the like, the subject of administration of the aptamer is not particularly limited and, for example, primates (e.g., human, monkey), rodents (e.g., mouse, rat, guinea pig), and companion animals, domestic animals and working animals (e.g., dog, cat, horse, bovine, goat, sheep, swine) can be mentioned.

The aptamer and complex of the present invention are capable of binding specifically to NGF. Therefore, the aptamer and complex of the present invention are useful as probes for NGF detection. The probes are useful in in vivo imaging of NGF, measurements of blood concentrations, tissue staining, ELISA and the like. The probes are also useful as diagnostic agents, test drugs, reagents and the like for diseases involving NGF (diseases accompanied by pain or inflammation, and the like).

Based on their specific binding to NGF, the aptamer and complex of the present invention can be used as ligands for separation and purification of NGF.

In addition, the aptamer and complex of the present invention can be used as test drugs for examining the mental condition of romance and the like, or medicaments, regulators, enhancers or mitigators for controlling the mental condition.

The aptamer and complex of the present invention can be used as drug delivery vehicles.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The medicament may be a rapid-release preparation or sustained-release preparation. Examples of sustained-release bases include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. Sustained-release preparations are also suitable preparations. The sustained-release preparations include sustained release from carriers or containers embedded in the body, such as artificial bones, biodegradable or non-degradable sponges, bags, drug pumps, osmotic pressure pumps and the like. Devices for continuous or intermittent, systemic or topical delivery from outside the body are also included in the scope of sustained-release preparations. Biodegradable bases include liposome, cationic liposome, poly(lactic-co-glycolic) acid (PLGA), atherocollagen, gelatin, hydroxyapatite, polysaccharide sizofuran. In addition to liquid injections and sustained release preparation, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monoleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicone substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying NGF.

The aptamer and the complex of the present invention can be immobilized onto a solid phase carrier by a method known per se. For example, a method that introduces an affinity substance (e.g., those described above) or a predetermined functional group into the aptamer (hydrophobic substance-added aptamer) or the complex of the present invention, and then immobilizes the aptamer and complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating NGF. In particular, the present invention makes it possible to separate NGF from the proteins of other family proteins. The method of purification and concentration of the present invention can comprise adsorbing NGF to the solid phase carrier of the present invention, and eluting the adsorbed NGF with an eluent. Adsorption of NGF to the solid phase carrier of the present invention can be achieved by a method known per se. For example, a NGF-containing sample (e.g., bacterial or cell culture or culture supernatant, blood) is introduced into the solid phase carrier of the present invention or a composition containing the same. NGF can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, urea, a chelating agent (e.g., EDTA), a potassium salt (e.g., KCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after NGF adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The present invention also provides a method of detecting and quantifying NGF. In particular, the present invention makes it possible to detect and quantify NGF separately from the proteins of other family proteins. The method of detection and quantitation of the present invention can comprise measuring NGF by utilizing the aptamer of the present invention (e.g., by the use of the complex and solid phase carrier of the present invention). The method of detecting and quantifying NGF can be performed in the same manner as an immunological method, except that the aptamer of the present invention is used in place of an antibody. Therefore, by using the aptamer of the present invention as a probe in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot technique, immunohistochemical staining method, and cell sorting method, detection and quantitation can be performed. The aptamer of the present invention can also be used as a molecular probe for PET and the like. These methods can be useful in, for example, measuring NGF contents in living organisms or biological samples, and in diagnosing a disease associated with NGF.

The disclosures in all publications mentioned herein, including patents and patent application specifications, are incorporated by reference herein in the present invention to the extent that all of them have been given expressly.

EXAMPLES

The present invention is hereinafter described in more detail by means of the following Examples, which, however, never limit the scope of the invention.

Example 1

RNA Aptamer (1) Production of RNA Aptamer

The sequence of RNA aptamer was determined based on the aptamer shown by SEQ ID NOs: 40, 60, 62, 67 and 68 described in PCT/JP09/066,457. These RNA aptamers were produced by a method using a transcriptase or chemical synthesis by a phosphoramidite method. Since chemical synthesize of long chain RNA is difficult, transcriptase was used for the production. To be specific, aptamers shown by aptamer IDs: 1-25 and aptamer IDs: 27-54 were obtained by transcription and aptamers shown by aptamer IDs: 26, 26(1)-(72), 29(1) and aptamer IDs: 55-63 were obtained by chemical synthesis.

Transcription was performed by producing the DNA of the object aptamer by chemical synthesis, and using DuraScribe (registered trade mark) T7 Transcription Kit (manufactured by Epicentre). The RNA obtained by this method has a fluorinated 2'-position of the ribose of the pyrimidine nucleotide. The transcription product was treated with DNase, the protein was removed by a phenol-chloroform treatment, and RNA was collected by ethanol precipitation. The purity of the recovered aptamer was confirmed by polyacrylamide electrophoresis, and the quantity was confirmed by an absorbance measurement method.

The chemical synthesis was performed by a phosphoramidite method. Chemical synthesis by a phosphoramidite method is a generally-employed method, which is as described in Nucleic Acid (Vol. 2) [1] Synthesis and Analysis of Nucleic Acid (Editor: Yukio Sugiura, Hirokawa Publishing Company) and the like. In fact, nucleic acid synthesizer (AB1394), manufactured by Applied Biosystems and the like, were used for the synthesis, and the synthesized product was purified by high performance liquid chromatography method (HPLC). The purity of the final synthetic substance was determined by HPLC, and not less than 85% passed. The molecular weight was confirmed by MALDI-TOFMS to be identical with the theoretical molecular weight.

An aptamer wherein polyethylene glycol chain (PEG) is added to the 5' terminal or 3' terminal was synthesized as follows. First, an aptamer added with a linker having an amino group at the 5' terminal or 3' terminal was synthesized using a nucleic acid synthesizer. For the 5' terminal, ssH Linker (SAFC) or DMS (O)MT-AMINO-MODIFIER C6 (GLENRESERCH) was used and for the 3' terminal, TFA Amino C-6 lcaa CPG (ChemGenes) was used. The aptamers added with these amino groups were purified by HPLC, and the purity was analyzed by HPLC and MALDI-TOFMS. Then, these aptamers were mixed with 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), or 4-branched TS type PEG having a molecular weight of 80000 (SUNBRIGHT GL4-800TS manufactured by NOF CORPORATION), each of which being added with N-hydroxysuccinimide active group, and reacted at room temperature to link PEG and the aptamer by an amide bond. After completion of the reaction, purification and purity analysis were performed by HPLC.

Examples of the partial structure of the thus-obtained aptamer of the present invention, wherein the terminal is modified with PEG, are shown below.

(1) a structure wherein aptamer is bound to 2-branched GS type PEG via ssH linker (Ta):
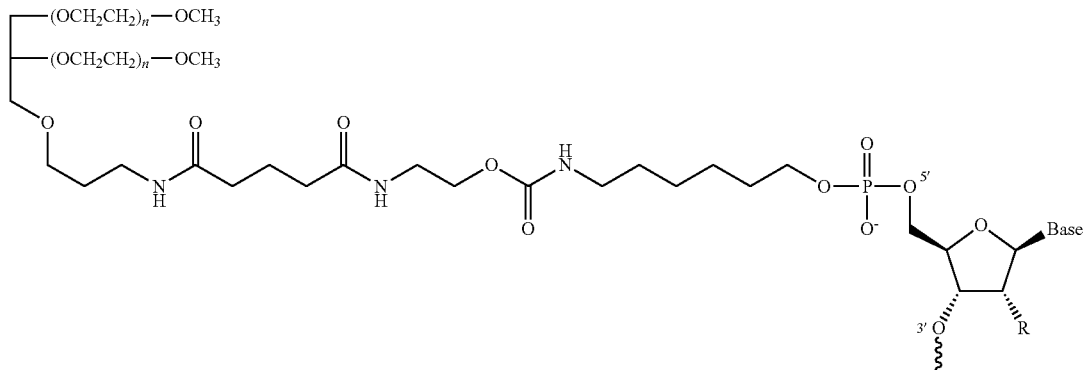
(2) a structure wherein aptamer is bound to 2-branched GS type PEG via TFA Amino C-6(Tc):
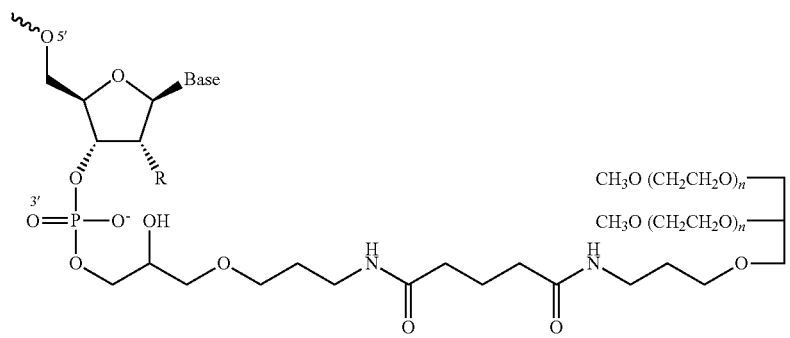
(3) a structure wherein aptamer is bound to 2-branched TS type PEG via ssH linker(Ta):
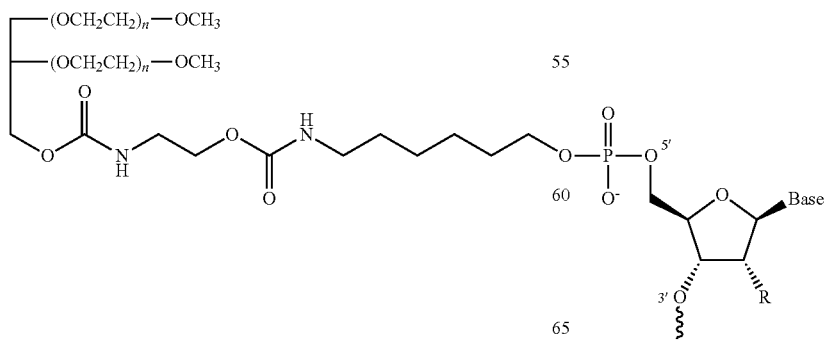

(4) a structure wherein aptamer is bound to 4-branched TS type PEG via ssH linker(Ta):

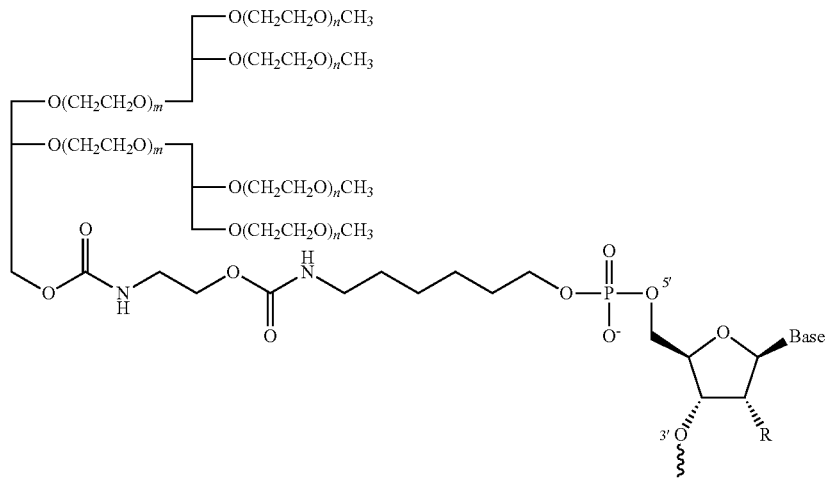

(5) a structure wherein aptamer is bound to 4-branched TS type PEG via DMS (O)MT-AMINO-MODIFIFIER C6(Tb):

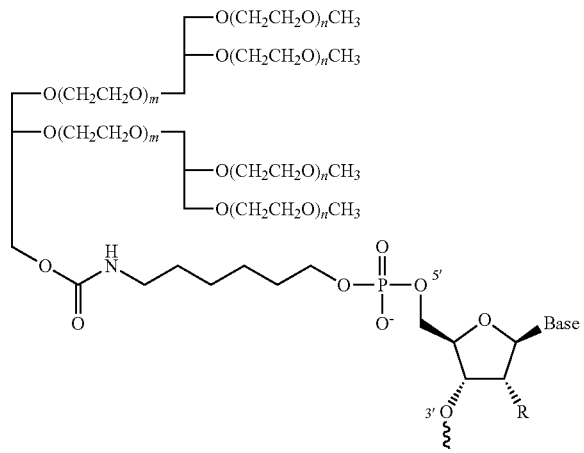

The nucleotides of the actually obtained aptamers represented by aptamer IDs: 1-54 are shown in the following Table 1.

Unless particularly indicated, the bond between nucleotides is a phosphodiester bond. The lower-case letters show RNA, higher-case letters show DNA, and s shows a phosphorothioate bond. The parentheses in nucleotide show modification at the 2'-position of ribose, F shows a fluorine atom, M shows an O-methyl group, and L shows Locked Nucleic Acid (LNA). For example, g(M) indicated in the following means g wherein the 2'-position is modified with O-methyl group. Ta shows the linker region when ssH linker is used for linking PEG and aptamer, Tb shows the linker region when DMS (O)MT-AMINO-MODIFIFIER C6 is used for linking PEG and aptamer, and Tc shows the linker region when TFA Amino C-6 is used for linking PEG and aptamer. idT shows inverted dT. PEG40GS2 is 2-branched GS type having a molecular weight of 40000 (SUNBRIGHT GL2-400GS2 manufactured by NOF CORPORATION), PEG40TS2 is 2-branched TS type having a molecular weight of 40000 (SUNBRIGHT GL2-400TS manufactured by NOF CORPORATION), PEG40TS4 is 4-branched TS type having a molecular weight of 40000 (SUNBRIGHT GL4-400TS manufactured by NOF CORPORATION), PEG80TS2 is 2-branched TS type having a molecular weight of 80000 (SUNBRIGHT GL2-800TS manufactured by NOF CORPORATION), and PEG80TS4 is 4-branched TS type having a molecular weight of 80000 (SUNBRIGHT GL4-800TS manufactured by NOF CORPORATION).

The aptamers shown by aptamer IDs: 1-30 contain a consensus sequence UGAAAGAAACC (SEQ ID NO: 67). The aptamers shown by aptamer IDs: 31-51 contain a consensus sequence CGAACAAAACU (SEQ ID NO: 68). The aptamers shown by aptamer IDs: 52, 53, 54 each contain a consensus sequences UGAAAAAAACC (SEQ ID NO: 66), CGAAAGAAACU (SEQ ID NO: 69).

TABLE 1

| aptamer ID | prepared aptamer | SEQ ID NO: |
|---|---|---|
| 1 | gggagaac(F)u(F)u(F)c(F)gac(F)c(F)agaag u(F)u(F)u(F)gaaagaaac(F)c(F)c(F)aaau (F)u(F)aaagu(F)gaac(F)agu(F)au(F)gu(F) gc(F)gc(F)au(F)ac(F)a | 1 |
| 2 | gggagaac(F)u(F)u(F)c(F)gac(F)c(F)agaag u(F)u(F)u(F)gaaagaaac(F)c(F)c(F)aaau (F)u(F)aaagu(F)gaagu(F)au(F)gu(F)gc(F) gc(F)au(F)ac(F)au(F)u(F)c(F)c(F)u(F)c (F)a | 2 |
| 3 | gggagaac(F)u(F)u(F)c(F)gac(F)c(F)agaag u(F)u(F)u(F)gaaagaaac(F)c(F)c(F)aaau (F)u(F)aaaggaac(F)agu(F)au(F)gu(F)gc (F)gc(F)au(F)ac(F)au(F)ggau(F)c(F)c(F) u(F)c(F)a | 3 |
| 4 | gggagaac(F)u(F)u(F)c(F)gac(F)c(F)agaag u(F)u(F)u(F)gaaagaaac(F)c(F)c(F)aaau (F)u(F)aaagu(F)gaac(F)agu(F)au(F)gu(F) gc(F)gc(F)au(F)ac(F)u(F)ggau(F)c(F)c (F)u(F)c(F)a | 4 |
| 5 | gggagaac(F)u(F)u(F)c(F)gac(F)c(F)agaag u(F)u(F)u(F)gaaagaaac(F)c(F)c(F)aaau (F)u(F)aaaaac(F)agu(F)au(F)gu(F)gc(F)g c(F)au(F)ac(F)a | 5 |

TABLE 1-continued

| aptamer ID | prepared aptamer | SEQ ID NO: |
|---|---|---|
| 6 | gggagaac(F)u(F)u(F)c(F)gac(F)c(F)agaag u(F)u(F)u(F)gaaagaaac(F)c(F)c(F)aaaaaa gu(F)gaac(F)agu(F)au(F)gu(F)gc(F)gc(F) au(F)ac(F)a | 6 |
| 7 | gggagaac(F)u(F)u(F)c(F)gac(F)c(F)agaag u(F)u(F)u(F)gaaagaaac(F)c(F)c(F)aaau (F)u(F)aaaggaagu(F)au(F)gu(F)gc(F)gc (F)au(F)ac(F)a | 7 |
| 8 | gggagaac(F)u(F)u(F)c(F)gac(F)c(F)agaag u(F)u(F)u(F)gaaagaaac(F)c(F)c(F)aaau (F)u(F)aaagu(F)gaac(F)agau(F)gu(F)gc (F)gc(F)au(F)c(F)a | 8 |
| 9 | gggagaac(F)u(F)u(F)c(F)gac(F)c(F)agaag u(F)u(F)u(F)gaaagaaac(F)c(F)c(F)aaau (F)u(F)aaaaagau(F)gu(F)gc(F)gc(F)au(F) c(F)a | 9 |
| 10 | gggagaac(F)u(F)u(F)c(F)gc(F)c(F)agaag u(F)u(F)u(F)gaaagaaac(F)c(F)c(F)aaau (F)u(F)aaaaagu(F)au(F)gu(F)gc(F)gc(F) au(F)ac(F)a | 10 |
| 11 | gggagaac(F)u(F)u(F)c(F)gc(F)c(F)agaag u(F)u(F)u(F)gaaagaaac(F)c(F)c(F)aaau (F)aaaaagu(F)au(F)gu(F)gc(F)gc(F)au (F)ac(F)a | 11 |
| 12 | gggagaac(F)u(F)u(F)c(F)gc(F)c(F)agaag u(F)u(F)u(F)gaaagaaac(F)c(F)c(F)aaau (F)u(F)aaagu(F)au(F)gu(F)gc(F)gc(F)a u(F)ac(F)a | 12 |
| 13 | gggagaac(F)u(F)u(F)c(F)gc(F)c(F)agaag u(F)u(F)u(F)gaaagaaac(F)c(F)c(F)aaau (F)u(F)aaagu(F)au(F)gu(F)gc(F)gc(F)au (F)ac(F)a | 13 |
| 14 | gggagaac(F)u(F)u(F)c(F)gc(F)c(F)agaag u(F)u(F)u(F)gaaagaaac(F)c(F)c(F)aau (F)u(F)aaaaagu(F)au(F)gu(F)gc(F)gc(F) au(F)ac(F)a | 14 |
| 15 | gggagaac(F)u(F)u(F)c(F)gc(F)c(F)agaag u(F)u(F)u(F)gaaagaaac(F)c(F)c(F)au(F) u(F)aaaagu(F)au(F)gu(F)gc(F)gc(F)au (F)ac(F)a | 15 |
| 16 | gggagaac(F)u(F)u(F)c(F)gc(F)c(F)agaag u(F)u(F)u(F)gaaagaaac(F)c(F)c(F)aaau (F)u(F)aaaaagau(F)gu(F)gc(F)gc(F)au (F)c(F)a | 16 |
| 17 | gggagaac(F)u(F)u(F)c(F)gc(F)c(F)agaag u(F)u(F)u(F)gaaagaaac(F)c(F)c(F)aaau (F)u(F)aaagau(F)gu(F)gc(F)gc(F)au(F)c (F)a | 17 |
| 18 | gggagaac(F)u(F)u(F)c(F)gc(F)c(F)agaag u(F)u(F)u(F)gaaagaaac(F)c(F)c(F)aaau (F)aaagau(F)gu(F)gc(F)gc(F)au(F)c(F)a | 18 |
| 19 | gggagaac(F)u(F)u(F)c(F)gc(F)c(F)agaag u(F)u(F)u(F)gaaagaaac(F)c(F)c(F)aaau (F)aaagau(F)gu(F)gc(F)gc(F)au(F)c(F) | 19 |
| 20 | gggagaac(F)u(F)u(F)c(F)gc(F)c(F)agaag u(F)u(F)u(F)gaaagaaac(F)c(F)c(F)aaau (F)aaagu(F)gu(F)gc(F)gc(F)ac(F)a | 20 |
| 21 | gggagaac(F)u(F)u(F)c(F)gc(F)c(F)agaag u(F)u(F)u(F)gaaagaaac(F)c(F)c(F)aaau (F)aaagagu(F)gc(F)gc(F)u(F)c(F)a | 21 |
| 22 | gggagac(F)u(F)c(F)gc(F)c(F)agagu(F)u (F)gaaagaaac(F)c(F)c(F)aaau(F)aaagau (F)gu(F)gc(F)gc(F)au(F)c(F)a | 22 |
| 23 | gggagaac(F)u(F)u(F)c(F)gc(F)c(F)agaag u(F)u(F)u(F)gaaagaaac(F)c(F)c(F)aaau (F)aagu(F)gu(F)gc(F)gc(F)ac(F)a | 23 |
| 24 | gggagaac(F)u(F)u(F)c(F)gc(F)c(F)agaag u(F)u(F)u(F)gaaagaaac(F)c(F)c(F)aaau (F)aagu(F)gu(F)gc(F)gc(F)ac(F) | 24 |
| 25 | gggagac(F)u(F)c(F)gc(F)c(F)agagu(F)u (F)gaaagaaac(F)c(F)c(F)aaau(F)aaagu (F)gu(F)gc(F)gc(F)ac(F)a | 25 |
| 26 | gggagac(F)u(F)c(F)gc(F)c(F)agagu(F)u (F)gaaagaaac(F)c(F)c(F)aaau(F)aagu(F) gu(F)gc(F)gc(F)ac(F) | 26 |
| 26(1) | idT-g(M)g(M)ga(M)ga(M)c(F)u(F)c(F)g (M)c(F)c(F)a(M)g(M)a(M)g(M)u(F)u(F)ga aaga(M)aa(M)c(F)c(F)c(F)a(M)a(M)a(M) u(F)a(M)a(M)g(M)u(F)g(M)u(F)g(M)c(F)g (M)c(F)a(M)c(F)-idT | 26 |
| 26(2) | idT-g(M)g(M)ga(M)ga(M)c(F)u(F)c(F)g (M)c(F)c(F)a(M)g(M)a(M)g(M)u(F)u(F)ga aag(M)aa(M)ac(F)c(F)c(F)a(M)a(M)a(M) u(F)a(M)a(M)g(M)u(F)g(M)u(F)g(M)c(F)g (M)c(F)a(M)c(F)-idT | 26 |
| 26(3) | gggaga(M)c(F)u(F)c(F)g(M)c(F)c(F)a(M) g(M)a(M)g(M)u(F)u(F)gaaagaaac(F)c(F)c (F)aaau(F)aagu(F)gu(F)gc(F)gc(F)ac(F) | 26 |
| 26(4) | g(M)g(M)ga(M)g(M)ac(F)u(F)c(F)gc(F)c (F)agagu(F)u(F)gaaag(M)a(M)a(M)ac (F)c(F)c(F)aaau(F)aagu(F)gu(F)gc(F)gc (F)ac(F) | 26 |
| 26(5) | gggagac(F)u(F)c(F)gc(F)c(F)agagu(F)u (F)gaaagaaac(F)c(F)c(F)a(M)a(M)a(M)u (F)a(M)a(M)gu(F)gu(F)gc(F)gc(F)ac(F) | 26 |
| 26(6) | gggagac(F)u(F)c(F)gc(F)c(F)agagu(F)u (F)gaaagaaac(F)c(F)c(F)aaau(F)aag(M)u (F)g(M)u(F)g(M)c(F)g(M)c(F)a(M)c(F) | 26 |
| 26(7) | gggagac(F)u(F)c(F)gc(F)c(F)agagu(F)u (F)gaa(M)agaaac(F)c(F)c(F)aaau(F)aagu (F)gu(F)gc(F)gc(F)ac(F) | 26 |
| 26(8) | gggagac(F)u(F)c(F)gc(F)c(F)agagu(F)u (F)gaaa(M)gaaac(F)c(F)c(F)aaau(F)aagu (F)gu(F)gc(F)gc(F)ac(F) | 26 |
| 26(9) | idT-g(M)g(M)ga(M)ga(M)c(F)u(F)c(F)g (M)c(F)c(F)a(M)g(M)a(M)g(M)u(F)u(F)ga aag(M)a(M)a(M)ac(F)c(F)c(F)a(M)a(M)a (M)u(F)a(M)a(M)g(M)u(F)g(M)u(F)g(M)c (F)g(M)c(F)a(M)c(F)-idT | 26 |
| 26(10) | idT-g(M)g(M)ga(M)ga(M)c(F)u(F)c(F)g (M)c(F)c(F)a(M)g(M)a(M)g(M)u(F)u(F)ga aag(M)aa(M)ac(F)c(F)c(F)a(M)a(M)a (M)u(F)a(M)a(M)g(M)u(F)g(M)u(F)g(M)c (F)g(M)c(F)a(M)c(F)-idT | 26 |
| 26(11) | idT-g(M)g(M)ga(M)ga(M)c(F)u(F)c(F)g (M)c(F)c(F)a(M)g(M)a(M)g(M)u(F)u(F)ga aag(M)a(M)a(M)c(F)c(F)c(F)a(M)a (M)a(M)u(F)a(M)a(M)g(M)u(F)g(M)u(F)g (M)c(F)g(M)c(F)a(M)c(F)-idT | 26 |

TABLE 1-continued

| aptamer ID | prepared aptamer | SEQ ID NO: |
|---|---|---|
| 26(12) | idT-g(M)g(M)ga(M)g(M)a(M)c(F)u(F)c(F)g(M)c(F)c(F)a(M)g(M)a(M)g(M)u(F)u(F)gaaag(M)aa(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(13) | idT-g(M)g(M)ga(M)ga(M)c(F)u(F)c(F)g(M)c(F)c(F)a(M)g(M)a(M)g(M)u(F)u(F)gaa(M)ag(M)aa(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(14) | idT-g(M)g(M)ga(M)ga(M)c(F)u(F)c(F)g(M)c(F)c(F)a(M)g(M)a(M)g(M)u(F)u(F)gaa(M)aa(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(15) | idT-g(M)g(M)ga(M)ga(M)c(F)u(F)c(F)g(M)c(F)c(F)a(M)g(M)a(M)g(M)u(F)u(F)ga(M)a(M)g(M)aa(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(16) | PEG40GS2-Ta-g(M)g(M)ga(M)ga(M)c(F)u(F)c(F)g(M)c(F)c(F)a(M)g(M)a(M)g(M)u(F)u(F)gaaag(M)aa(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(17) | idT-g(M)g(M)ga(M)ga(M)c(F)u(F)c(F)g(M)c(F)c(F)a(M)g(M)a(M)g(M)u(F)u(F)gaaag(M)aa(M)ac(F)c(F)c(F)a(M)a(M)a(M)u(F)a(M)a(M)g(M)u(F)g(M)u(F)g(M)c(F)g(M)c(F)a(M)c(F)-Tc-PEG40GS2 | 26 |
| 26(18) | idT-g(M)g(M)ga(M)ga(M)g(M)a(M)c(F)u(F)c(F)g(M)c(F)c(F)a(M)g(M)a(M)g(M)u(F)u(F)aa(M)a(M)g(M)a(M)a(M)a(M)c(F)c(F)c(F)a(M)a(M)a(M)u(F)a(M)a(M)g(M)u(F)g(M)u(F)g(M)c(F)g(M)c(F)a(M)c(F)-idT | 26 |
| 26(19) | idT-g(M)g(M)ga(M)ga(M)g(M)a(M)c(F)u(F)c(F)g(M)c(F)c(F)a(M)g(M)a(M)g(M)u(F)u(F)ga(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(20) | idT-g(M)g(M)ga(M)ga(M)g(M)a(M)c(F)u(F)c(F)g(M)c(F)c(F)a(M)g(M)a(M)g(M)u(F)u(F)ga(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(21) | idT-g(M)g(M)ga(M)g(M)g(M)a(M)Cu(F)c(F)g(M)c(F)c(F)a(M)g(M)a(M)g(M)u(F)u(F)ga(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(22) | idT-g(M)g(M)ga(M)g(M)a(M)g(M)a(M)c(F)Tc(F)g(M)c(F)c(F)a(M)g(M)a(M)g(M)u(F)u(F)ga(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(23) | idT-g(M)g(M)ga(M)g(M)a(M)g(M)a(M)c(F)u(F)Cg(M)c(F)c(F)a(M)g(M)a(M)g(M)u(F)u(F)ga(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(24) | idT-g(M)g(M)ga(M)g(M)a(M)c(F)u(F)c(F)g(M)Cc(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(25) | idT-g(M)g(M)ga(M)g(M)a(M)c(F)u(F)c(F)g(M)c(F)Ca(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(26) | idT-g(M)g(M)ga(M)g(M)a(M)c(F)u(F)c(F)g(M)c(F)c(F)a(M)g(M)a(M)g(M)Tu(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(27) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)Ca(M)a(M)a(M)u(F)a(M)a(M)g(M)u(F)g(M)u(F)g(M)c(F)g(M)c(F)a(M)c(F)-idT | 26 |
| 26(28) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)Ta(M)a(M)g(M)u(F)g(M)u(F)g(M)c(F)g(M)c(F)a(M)c(F)-idT | 26 |
| 26(29) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)Tg(M)u(F)g(M)c(F)g(M)c(F)a(M)c(F)-idT | 26 |
| 26(30) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)C-idT | 26 |
| 26(31) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(32) | idT-g(M)g(M)ga(M)g(M)a(M)c(F)u(F)c(F)g(M)c(M)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(33) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(34) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(F)-idT | 26 |
| 26(35) | idT-g(M)g(M)ga(M)g(M)a(M)c(F)u(F)c(F)g(M)c(F)c(F)a(M)g(M)a(M)g(M)u(F)u(F)gaa(M)a(M)g(M)a(M)a(M)ac(F)c(F)c(F)a(M)a(M)a(M)u(F)a(M)a(M)g(M)u(F)g(M)u(F)g(M)c(F)g(M)c(F)a(M)c(M)-idT | 26 |

TABLE 1-continued

| aptamer ID | prepared aptamer | SEQ ID NO: |
|---|---|---|
| 26(36) | idT-g(M)g(M)gsa(M)g(M)a(M)c(M)u(F)c(F)g(M)c(F)c(F)a(M)g(M)a(M)g(M)u(F)u(F)gaa(M)a(M)g(M)a(M)a(M)ac(F)c(F)c(F)a(M)a(M)u(F)a(M)a(M)g(M)u(F)g(M)u(F)g(M)c(F)g(M)c(F)a(M)c(F)-idT | 26 |
| 26(37) | idT-g(M)g(M)ga(M)g(M)a(M)c(M)u(F)c(F)g(M)c(F)c(F)a(M)g(M)a(M)g(M)u(F)u(F)sgaa(M)a(M)g(M)a(M)a(M)ac(F)c(F)c(F)a(M)a(M)u(F)a(M)a(M)g(M)u(F)g(M)u(F)g(M)c(F)g(M)c(F)a(M)c(F)-idT | 26 |
| 26(38) | idT-g(M)g(M)ga(M)g(M)a(M)c(M)u(F)c(F)g(M)c(F)c(F)a(M)g(M)a(M)g(M)u(F)u(F)gasa(M)a(M)g(M)a(M)a(M)ac(F)c(F)c(F)a(M)a(M)u(F)a(M)a(M)g(M)u(F)g(M)u(F)g(M)c(F)g(M)c(F)a(M)c(F)-idT | 26 |
| 26(39) | idT-g(M)g(M)ga(M)g(M)a(M)c(M)u(F)c(F)g(M)c(F)c(F)a(M)g(M)a(M)g(M)u(F)u(F)gaa(M)a(M)g(M)a(M)a(M)sac(F)c(F)c(F)a(M)a(M)u(F)a(M)a(M)g(M)u(F)g(M)u(F)g(M)c(F)g(M)c(F)a(M)c(F)-idT | 26 |
| 26(40) | idT-g(M)g(M)ga(M)g(M)a(M)c(M)u(F)c(F)g(M)c(F)c(F)a(M)g(M)a(M)g(M)u(F)u(F)gaa(M)a(M)g(M)a(M)a(M)asc(F)c(F)c(F)a(M)a(M)u(F)a(M)a(M)g(M)u(F)g(M)u(F)g(M)c(F)g(M)c(F)a(M)c(F)-idT | 26 |
| 26(41) | idT-g(M)g(M)ga(M)g(M)a(M)c(M)u(F)c(F)g(M)c(F)c(F)a(M)g(M)a(M)g(M)u(F)u(F)gaa(M)a(M)g(M)a(M)a(M)ac(F)c(F)Ca(M)a(M)a(M)u(F)a(M)a(M)g(M)Tg(M)u(F)g(M)c(F)g(M)c(F)a(M)c(F)-idT | 26 |
| 26(42) | idT-g(M)g(M)ga(M)g(M)a(M)c(F)u(F)Cg(M)c(F)c(F)a(M)g(M)a(M)g(M)u(F)u(F)gaa(M)a(M)g(M)a(M)a(M)ac(F)c(F)Ca(M)a(M)a(M)Ta(M)a(M)g(M)Tg(M)u(F)g(M)c(F)g(M)c(F)a(M)c(F)-idT | 26 |
| 26(43) | idT-g(M)g(M)ga(M)g(M)a(M)CTCg(M)CCa(M)g(M)a(M)g(M)Tu(F)gaa(M)a(M)g(M)a(M)a(M)ac(F)c(F)Ca(M)a(M)a(M)Ta(M)a(M)g(M)Tg(M)u(F)g(M)c(F)g(M)c(F)a(M)C-idT | 26 |
| 26(44) | idT-g(M)g(M)ga(M)g(M)a(M)c(M)u(F)c(F)g(M)c(M)c(M)a(M)g(M)a(M)g(M)u(M)u(F)gaa(M)a(M)g(M)a(M)a(M)ac(F)c(F)c(F)a(M)a(M)a(M)u(M)a(M)a(M)g(M)u(F)g(M)u(F)g(M)c(F)g(M)c(F)a(M)c(M)-idT | 26 |
| 26(45) | idT-g(M)g(M)ga(M)g(M)a(M)c(M)u(F)c(M)g(M)c(M)c(M)a(M)g(M)a(M)g(M)u(M)u(F)gaa(M)a(M)g(M)a(M)a(M)ac(F)c(F)c(F)a(M)a(M)a(M)u(M)a(M)a(M)g(M)u(F)g(M)u(F)g(M)c(F)g(M)c(F)a(M)c(M)-idT | 26 |
| 26(46) | idT-g(M)g(M)ga(M)g(M)a(M)c(M)u(M)c(F)g(M)c(M)c(M)a(M)g(M)a(M)g(M)u(M)u(F)gaa(M)a(M)g(M)a(M)a(M)ac(F)c(F)c(F)a(M)a(M)a(M)u(M)a(M)a(M)g(M)u(F)g(M)u(F)g(M)c(F)g(M)c(F)a(M)c(M)-idT | 26 |
| 26(47) | idT-g(M)g(M)ga(M)g(M)a(M)c(M)u(F)c(F)g(M)c(M)c(M)a(M)g(M)a(M)g(M)u(M)u(F)gaa(M)a(M)g(M)a(M)a(M)ac(F)c(F)c(F)a(M)a(M)a(M)u(M)a(M)a(M)g(M)u(F)g(M)u(F)g(M)c(F)g(M)c(F)a(M)c(M)-idT | 26 |
| 26(48) | idT-g(M)g(M)ga(M)g(M)a(M)c(M)u(F)c(F)g(M)c(M)c(M)a(M)g(M)a(M)g(M)u(M)u(M)gaa(M)a(M)g(M)a(M)a(M)ac(F)c(F)c(F)a(M)a(M)a(M)u(M)a(M)a(M)g(M)u(M)g(M)u(F)g(M)c(F)g(M)c(F)a(M)c(M)-idT | 26 |
| 26(49) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)c(F)a(M)a(M)a(M)u(M)a(M)a(M)g(M)u(M)g(M)u(F)g(M)c(F)g(M)c(F)a(M)c(M)-idT | 26 |
| 26(50) | idT-g(M)g(M)ga(M)g(M)a(M)c(M)TCg(M)c(M)c(M)a(M)g(M)a(M)a(M)ac(F)c(F)Ca(M)a(M)a(M)u(M)a(M)a(M)g(M)Tg(M)c(F)g(M)c(F)a(M)c(M)-idT | 26 |
| 26(51) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)c(F)c(F)c(F)a(M)a(M)u(M)a(M)a(M)g(M)u(M)g(M)u(F)g(M)c(F)g(M)c(F)a(M)c(M)-idT | 26 |
| 26(52) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)c(F)a(M)a(M)a(M)u(M)a(M)a(M)g(M)u(M)g(M)u(F)g(M)c(F)g(M)c(F)a(M)c(M)-idT | 26 |
| 26(53) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)Ac(F)c(F)c(F)a(M)a(M)a(M)u(M)a(M)a(M)g(M)u(M)g(M)u(F)g(M)c(F)g(M)c(F)a(M)c(M)-idT | 26 |
| 26(54) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)aCc(F)Ca(M)a(M)a(M)u(M)a(M)a(M)g(M)u(M)g(M)u(F)g(M)c(F)g(M)c(F)a(M)c(M)-idT | 26 |
| 26(55) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)Ca(M)a(M)a(M)u(M)a(M)a(M)g(M)u(M)g(M)Tg(M)c(F)g(M)c(F)a(M)c(M)-idT | 26 |
| 26(56) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)Ca(M)a(M)a(M)u(M)a(M)a(M)g(M)u(M)g(M)Ug(M)c(F)g(M)c(F)a(M)c(M)-idT | 26 |
| 26(57) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)Ca(M)a(M)a(M)u(M)a(M)a(M)g(M)u(M)g(M)g(M)u(F)g(M)Cg(M)c(F)a(M)c(M)-idT | 26 |
| 26(58) | idT-g(M)g(M)ga(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)Ca(M)a(M)a(M)u(M)a(M)a(M)g(M)u(M)g(M)g(M)u(F)g(M)c(F)g(M)Ca(M)c(M)-idT | 26 |
| 26(59) | idT-g(M)g(M)ga(M)g(F)a(M)g(M)a(M)c(M)u(M)c(M)g(M)c(M)c(M)a(M)g(M)a(M)g(M)u(M)u(M)gaa(M)a(M)g(M)a(M)a(M)ac(F)c(F)c(F)a(M)a(M)u(M)a(M)a(M)g(M)u(M)g(M)u(F)g(M)c(F)g(M)c(F)a(M)c(M)-idT | 26 |

TABLE 1-continued

| aptamer ID | prepared aptamer | SEQ ID NO: |
|---|---|---|
| 26(60) | idT-g(M)g(M)ga(M)g(M)a(M)c(M)u(M)c(M) g(M)c(M)c(M)a(M)g(M)a(M)g(M)u(M)u(M)g aa(M)a(M)g(M)a(M)a(M)a(M)(F)c(F)c(F) a(M)a(M)a(M)u(M)a(M)a(M)g(M)u(M)g(M) u(F)g(M)c(F)g(M)c(F)a(M)c(M)-idT | 26 |
| 26(61) | idT-g(M)g(M)ga(M)g(M)a(M)c(M)u(M)c(M) g(M)c(M)c(M)a(M)g(M)a(M)g(M)u(M)u(M)g aa(M)a(M)g(M)a(M)a(M)ac(F)c(F)c (L) a (M)a(M)a(M)u(M)a(M)a(M)g(M)u(M)g(M)u (F)g(M)c(F)g(M)c(F)a(M)c(M)-idT | 26 |
| 26(62) | idT-g(M)g(M)ga(M)g(M)a(M)c(M)u(M)c(M) g(M)c(M)c(M)a(M)g(M)a(M)g(M)u(M)u(M)g aa(M)a(M)g(M)a(M)a(M)a(L)c(F)c(F)c(F) a(M)a(M)a(M)u(M)a(M)a(M)g(M)u(M)g(M) u(F)g(M)c(F)g(M)c(F)a(M)c(M)-idT | 26 |
| 26(63) | idT-g(M)g(M)ga(M)g(M)a(M)c(M)u(M)c(M) g(M)c(M)c(M)a(M)g(M)a(M)g(M)u(M)u(M)g aa(M)a(M)g(M)a(M)a(M)aCc(F)Ca(M)a(M)a (M)u(M)a(M)a(M)g(M)u(M)g(M)u(M)g(M)c (F)g(M)c(F)a(M)c(M)-idT | 26 |
| 26(64) | PEG80TS4-Ta-g(M)g(M)ga(M)g(M)a(M)c(M) u(M)c(M)g(M)c(M)c(M)a(M)g(M)a(M)g(M)u (M)u(M)gaa(M)a(M)g(M)a(M)a(M)a(M)ac(F)c (F)c(F)a(M)a(M)a(M)u(M)a(M)a(M)g(M)u (M)g(M)u(M)g(M)c(F)g(M)c(F)a(M)c(M)-idT | 26 |
| 26(65) | PEG80TS4-Ta-g(M)g(M)ga(M)g(M)a(M)c(M) u(M)c(M)g(M)c(M)c(M)a(M)g(M)a(M)g(M)u (M)u(M)gaa(M)a(M)g(M)a(M)a(M)a(M)aCc(F)Ca (M)a(M)a(M)u(M)a(M)a(M)g(M)u(M)g(M)u (M)g(M)c(F)g(M)c(F)a(M)c(M)-idT | 26 |
| 26(66) | PEG40GS2-Ta-g(M)g(M)ga(M)g(M)a(M)c(F) u(F)c(F)g(M)c(F)c(F)a(M)g(M)a(M)g(M)u (M)u(F)gaa(M)a(M)g(M)a(M)a(M)ac(F)c (F)c(F)a(M)a(M)a(M)u(M)a(M)a(M)g(M)u(M) (F)g(M)u(F)g(M)c(F)g(M)c(F)a(M)c(F)- idT | 26 |
| 26(67) | PEG40TS2-Ta-g(M)g(M)ga(M)g(M)a(M)c(F) u(F)c(F)g(M)c(F)c(F)a(M)g(M)a(M)g(M)u(M) (F)u(F)gaa(M)a(M)g(M)a(M)a(M)ac(F)c (F)c(F)a(M)a(M)a(M)u(M)a(M)a(M)g(M)u (F)g(M)u(F)g(M)c(F)g(M)c(F)a(M)c(F)- idT | 26 |
| 26(68) | PEG80TS2-Ta-g(M)g(M)ga(M)g(M)a(M)c(F) u(F)c(F)g(M)c(F)c(F)a(M)g(M)a(M)g(M)u(M) (F)u(F)gaa(M)a(M)g(M)a(M)a(M)ac(F)c (F)c(F)a(M)a(M)a(M)u(M)a(M)a(M)g(M)u (F)g(M)u(F)g(M)c(F)g(M)c(F)a(M)c(F)- idT | 26 |
| 26(69) | PEG40TS4-Ta-g(M)g(M)ga(M)g(M)a(M)c(F) u(F)c(F)g(M)c(F)c(F)a(M)g(M)a(M)g(M)u(M) (F)u(F)gaa(M)a(M)g(M)a(M)a(M)ac(F)c (F)c(F)a(M)a(M)a(M)u(F)a(M)a(M)g(M)u (F)g(M)u(F)g(M)c(F)g(M)c(F)a(M)c(F)- idT | 26 |
| 26(70) | PEG80TS4-Ta-g(M)g(M)ga(M)g(M)a(M)c(F) u(F)c(F)g(M)c(F)c(F)a(M)g(M)a(M)g(M)u(M) (F)u(F)gaa(M)a(M)g(M)a(M)a(M)ac(F)c (F)c(F)a(M)a(M)a(M)u(F)a(M)a(M)g(M)u (F)g(M)u(F)g(M)c(F)g(M)c(F)a(M)c(F)- idT | 26 |
| 26(71) | PEG80TS4-Tb-g(M)g(M)ga(M)g(M)a(M)c(M) u(M)c(M)g(M)c(M)c(M)a(M)g(M)a(M)g(M)u (M)u(M)gaa(M)a(M)g(M)a(M)a(M)a(M)ac(F)c (F)c(F)a(M)a(M)a(M)u(M)a(M)a(M)g(M)u (M)g(M)u(M)g(M)c(F)g(M)c(F)a(M)c(M)- idT | 26 |
| 26(72) | PEG80TS4-Tb-g(M)g(M)ga(M)g(M)a(M)c(M) u(M)c(M)g(M)c(M)c(M)a(M)g(M)a(M)g(M)u (M)u(M)gaa(M)a(M)g(M)a(M)a(M)aCc(F)Ca (M)a(M)a(M)u(M)a(M)a(M)g(M)u(M)g(M)u (M)g(M)c(F)g(M)c(F)a(M)c(M)-idT | 26 |
| 27 | gggagac(F)u(F)c(F)gc(F)agagu(F)u(F)ga aagaaac(F)c(F)c(F)aaau(F)aagu(F)gu (F)gc(F)gc(F)ac(F)a | 27 |
| 28 | gggagac(F)u(F)c(F)gc(F)agagu(F)u(F)ga aagaaac(F)c(F)c(F)aaau(F)aagu(F)gu(F) gc(F)gc(F)ac(F) | 28 |
| 29 | gggagac(F)u(F)c(F)gc(F)c(F)agagu(F)u (F)gaaagaaac(F)c(F)c(F)aaau(F)agu(F)g u(F)gc(F)gc(F)ac(F) | 29 |
| 29(1) | idT-g(M)g(M)ga(M)g(M)a(M)c(F)u(F)c(F) g(M)c(F)c(F)a(M)g(M)a(M)g(M)u(F)u(F)g aa(M)a(M)g(M)a(M)a(M)a(M)c(F)c(F)c(F) a(M)a(M)a(M)u(F)a(M)g(M)u(F)g(M)u(F)g (M)c(F)g(M)c(F)a(M)c(F)-idT | 29 |
| 30 | gggagac(F)u(F)c(F)gc(F)agagu(F)u(F)ga aagaaac(F)c(F)c(F)aaau(F)agu(F)gu(F)g c(F)gc(F)ac(F) | 30 |
| 31 | gggagaac(F)u(F)u(F)c(F)gac(F)c(F)agaa gu(F)c(F)gau(F)aac(F)gaac(F)aaaac(F)u (F)c(F)c(F)c(F)aaaggaau(F)au(F)au(F)g u(F)gc(F)gc(F)au(F)ac(F)au(F)ggau(F) | 31 |
| 32 | gggagaac(F)u(F)u(F)c(F)gac(F)c(F)agaa gu(F)c(F)gau(F)aac(F)gaac(F)aaaac(F)u (F)c(F)c(F)c(F)aaaggaau(F)au(F)au(F)g u(F)gc(F)gc(F)au(F)ac(F)a | 32 |
| 33 | gggagaac(F)u(F)u(F)c(F)gac(F)c(F)agaa gu(F)c(F)gau(F)aac(F)gaac(F)aaaac(F)u (F)c(F)c(F)c(F)aaaggaau(F)au(F)au(F)g u(F)gc(F)gc(F)au(F)ac(F)au(F)ggau(F)c (F)c(F)u(F) | 33 |
| 34 | gggagaac(F)u(F)u(F)c(F)gac(F)c(F)agaa gu(F)c(F)gau(F)aac(F)gaac(F)aaaac(F)u (F)c(F)c(F)c(F)aaaggaau(F)au(F)gu(F)g c(F)gc(F)au(F)ac(F)a | 34 |
| 35 | gggagaac(F)u(F)u(F)c(F)gac(F)c(F)agaa gu(F)c(F)gau(F)aac(F)gaac(F)aaaac(F)u (F)c(F)c(F)c(F)aaaggu(F)au(F)au(F)gu (F)gc(F)gc(F)au(F)ac(F)a | 35 |
| 36 | gggagaac(F)u(F)u(F)c(F)gac(F)c(F)agaa gu(F)c(F)gau(F)aac(F)gaac(F)aaaac(F)u (F)c(F)c(F)c(F)aaaaau(F)au(F)gu(F) gc(F)gc(F)au(F)ac(F)a | 36 |
| 37 | gggagaac(F)u(F)u(F)c(F)gac(F)c(F)agaa gu(F)c(F)gau(F)aac(F)gaac(F)aaaac(F)u (F)c(F)c(F)c(F)ggaau(F)au(F)au(F)gu (F)gc(F)gc(F)au(F)ac(F)a | 37 |
| 38 | gggagaac(F)u(F)u(F)c(F)gac(F)c(F)agaa gu(F)c(F)gau(F)aac(F)gaac(F)aaaac(F)u (F)c(F)c(F)c(F)aaaggaau(F)au(F)au(F)g u(F)gc(F)gc(F)au(F)ac(F) | 38 |

TABLE 1-continued

| aptamer ID | prepared aptamer | SEQ ID NO: |
|---|---|---|
| 39 | gggagaac(F)u(F)u(F)c(F)gac(F)c(F)agaa gu(F)c(F)gau(F)aac(F)gaac(F)aaaac(F)u (F)c(F)c(F)c(F)aaaggaaau(F)gu(F)gc(F) gc(F)au(F)ac(F)a | 39 |
| 40 | gggagaac(F)u(F)u(F)c(F)gac(F)c(F)agaa gu(F)c(F)gau(F)aac(F)gaac(F)aaaac(F)u (F)c(F)c(F)c(F)aaau(F)au(F)au(F)gu(F) gc(F)gc(F)au(F)ac(F)a | 40 |
| 41 | gggagaac(F)u(F)u(F)c(F)gac(F)c(F)agaa gu(F)c(F)gau(F)aac(F)gaac(F)aaaac(F)u (F)c(F)c(F)c(F)aaaggu(F)aau(F)gu(F)gc (F)gc(F)au(F)ac(F)a | 41 |
| 42 | gggagaac(F)u(F)u(F)c(F)gac(F)c(F)agaa gu(F)c(F)gau(F)aac(F)gaac(F)aaaac(F)u (F)c(F)c(F)c(F)ggaau(F)aau(F)gu(F)gc (F)gc(F)au(F)ac(F)a | 42 |
| 43 | gggagaac(F)u(F)u(F)c(F)gac(F)c(F)agaa gu(F)c(F)gau(F)aac(F)gaac(F)aaaac(F)u (F)c(F)c(F)c(F)aaau(F)au(F)gu(F)gc(F) gc(F)au(F)ac(F)a | 43 |
| 44 | gggagaac(F)u(F)u(F)c(F)gac(F)c(F)agaa gu(F)c(F)gau(F)aac(F)gaac(F)aaaac(F)u (F)c(F)c(F)c(F)aaaggau(F)gu(F)gc(F)gc (F)au(F)ac(F)a | 44 |
| 45 | gggagaac(F)u(F)u(F)c(F)gac(F)c(F)agaa gu(F)c(F)gau(F)aac(F)gaac(F)aaaac(F)u (F)c(F)c(F)c(F)aaau(F)aau(F)gu(F)gc (F)gc(F)au(F)ac(F)a | 45 |
| 46 | gggagaac(F)u(F)u(F)c(F)gac(F)c(F)agaa gu(F)c(F)gau(F)aac(F)gaac(F)aaaac(F)u (F)c(F)c(F)c(F)aaau(F)au(F)gu(F)gc(F) gc(F)au(F)ac(F) | 46 |
| 47 | gggagaac(F)u(F)u(F)c(F)gac(F)c(F)agag u(F)c(F)gau(F)aac(F)gaac(F)aaaac(F)u (F)c(F)c(F)c(F)aaau(F)au(F)gu(F)gc(F) gc(F)au(F)ac(F)a | 47 |
| 48 | gggagaac(F)u(F)u(F)c(F)gac(F)c(F)agag u(F)c(F)gau(F)aac(F)gaac(F)aaaac(F)u (F)c(F)c(F)c(F)aaau(F)au(F)gu(F)gc(F) gc(F)au(F)ac(F) | 48 |
| 49 | gggagaac(F)u(F)u(F)c(F)gac(F)c(F)agaa gu(F)c(F)gau(F)aac(F)gaac(F)aaaac(F)u (F)c(F)c(F)c(F)aaau(F)au(F)gu(F)gc(F)g c(F)au(F)ac(F)a | 49 |
| 50 | gggagaac(F)u(F)u(F)c(F)gac(F)c(F)agag u(F)c(F)gau(F)aac(F)gaac(F)aaaac(F)u (F)c(F)c(F)c(F)aaau(F)au(F)gu(F)gc(F)g c(F)au(F)ac(F) | 50 |
| 51 | ggagaac(F)u(F)u(F)c(F)gac(F)c(F)agagu (F)c(F)gau(F)aac(F)gaac(F)aaaac(F)u (F)c(F)c(F)aaau(F)au(F)gu(F)gc(F)gc (F)au(F)ac(F) | 51 |
| 52 | gggagaac(F)u(F)u(F)c(F)gac(F)c(F)agaa gu(F)u(F)u(F)gaaaaaaac(F)c(F)c(F)aaau (F)u(F)aaagu(F)au(F)gu(F)gc(F)gc(F)au (F)ac(F)a | 52 |
| 53 | gggagaac(F)u(F)u(F)c(F)gac(F)c(F)agag u(F)c(F)gagagc(F)gaaagaaac(F)u(F)c(F) c(F)c(F)aaau(F)au(F)gu(F)gc(F)gc(F)au (F)ac(F) | 53 |
| 54 | gggagaac(F)u(F)u(F)c(F)gac(F)c(F)agaa gau(F)u(F)u(F)gaaaaaaac(F)c(F)c(F)aaa u(F)u(F)aaagu(F)au(F)gu(F)gc(F)gc(F)a u(F)ac(F)a | 54 |

(2) Production of Cholesterol-Added Aptamer

Based on the aptamer shown by SEQ ID NO: 30(6) described in PCT/JP09/066,457, an aptamer added with cholesterol at the 5' terminal was produced. The cholesterol-added aptamer was produced by chemical synthesis by a phosphoramidite method. As cholesterol, cholesterol amidite manufactured by ChemGenes (TEG cholesterol, non-DMT, CLP-2704) was used.

One example of the structure of the obtained cholesterol-added aptamer is shown below.

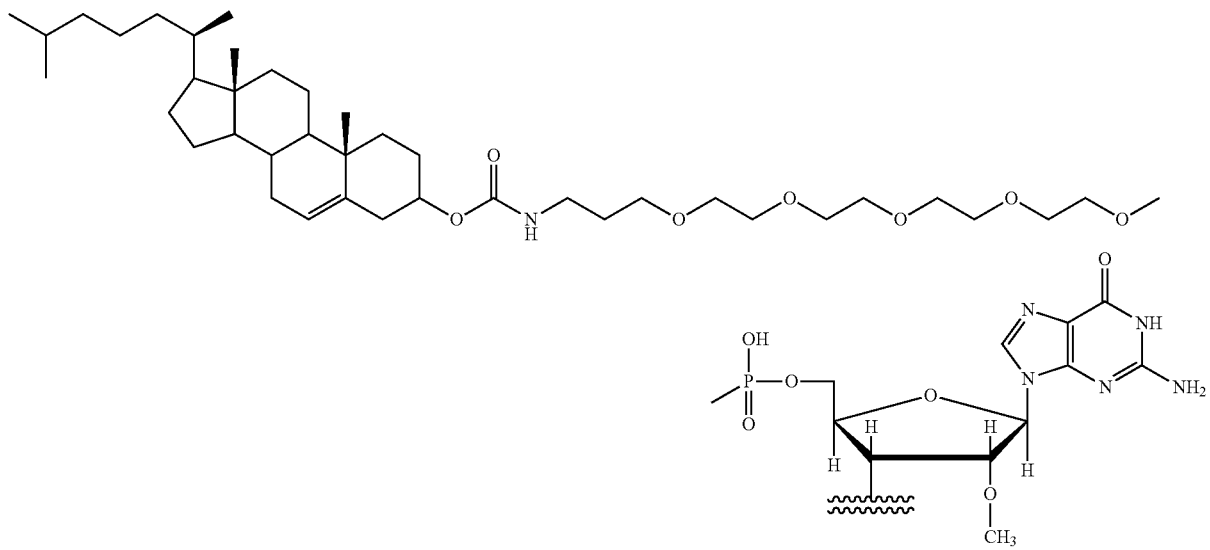

Actually obtained aptamers represented by aptamer IDs: 55-63 are shown in the following Table 2. Unless particularly indicated, the bond between nucleotides is a phosphodiester bond. The lower-case letters show RNA, higher-case letters show DNA. The parentheses in nucleotide show modification at the 2'-position of ribose, F shows a fluorine atom, M shows an O-methyl group. s shows a phosphorothioate bond. For example, g(M)sT indicated in the following means that T and g wherein the 2'-position is modified with O-methyl group are linked by a phosphorothioate bond. Chol shows cholesterol, and idT shows inverted dT. Aptamers represented by aptamer IDs: 55-63 characteristically have cholesterol on the 5' terminal.

TABLE 2

| aptamer ID | prepared aptamer | SEQ ID NO: |
|---|---|---|
| 55 | Chol-g(M)g(M)g(M)au(F)a(M)aa(M)a(M)a (M)u(F)a(M)g(M)a(M)g(M)u(F)u(F)u(F)g (M)a(M)u(F)a(M)a(M)a(M)c(F)a(M)c(F)c (F)u(F)gu(F)a(M)u(F)u(F)a(M)a(M)a(F)a (F)c(F)c(F)c(F)-idT | 55 |
| 56 | Chol-g(M)g(M)g(M)au(F)a(M)aa(M)a(M)a (M)u(F)a(M)g(M)a(M)g(M)u(F)u(F)u(F)g (M)a(M)Ta(M)a(M)a(M)c(F)a(M)c(F)c(F)u (F)gu(F)a(M)u(F)u(F)a(M)a(M)a(F)a(F)c (F)c(F)c(F)-idT | 56 |
| 57 | Chol-g(M)g(M)g(M)au(F)a(M)aa(M)a(M)a (M)u(F)a(M)g(M)a(M)g(M)Tu(F)u(F)g(M)a (M)Ta(M)a(M)a(M)c(F)a(M)c(F)c(F)u(F)g u(F)a(M)u(F)u(F)a(M)a(M)a(F)a(F)c(F)c (F)c(F)-idT | 57 |
| 57(1) | Chol-g(M)g(M)g(M)au(F)a(M)aa(M)a(M)a (M)u(F)a(M)g(M)a(M)g(M)sTu(F)u(F)g(M) a(M)Ta(M)a(M)a(M)c(F)a(M)c(F)c(F)u(F) gu(F)a(M)u(F)u(F)a(M)a(M)a(F)a(F)c(F) c(F)c(F)-idT | 57 |
| 57(2) | Chol-g(M)g(M)g(M)au(F)a(M)aa(M)a(M)a (M)u(F)a(M)g(M)a(M)g(M)Tsu(F)u(F)g(M) a(M)Ta(M)a(M)a(M)c(F)a(M)c(F)c(F)u(F) gu(F)a(M)u(F)u(F)a(M)a(M)a(F)a(F)c(F) c(F)c(F)-idT | 57 |
| 57(3) | Chol-g(M)g(M)g(M)au(F)a(M)aa(M)a(M)a (M)u(F)a(M)g(M)a(M)g(M)Tu(F)u(F)g(M)s a(M)Ta(M)a(M)a(M)c(F)a(M)c(F)c(F)u(F) gu(F)a(M)u(F)u(F)a(M)a(M)a(F)a(F)c(F) c(F)c(F)-idT | 57 |
| 57(4) | Chol-g(M)g(M)g(M)au(F)a(M)aa(M)a(M)a (M)u(F)a(M)g(M)a(M)g(M)Tu(F)u(F)g(M)a (M)sTa(M)a(M)a(M)c(F)a(M)c(F)c(F)u(F) gu(F)a(M)u(F)u(F)a(M)a(M)a(F)a(F)c(F) c(F)c(F)-idT | 57 |
| 57(5) | Chol-g(M)g(M)g(M)au(F)a(M)aa(M)a(M)a (M)u(F)a(M)g(M)a(M)g(M)Tu(F)u(F)g(M)a (M)Tsa(M)a(M)a(M)c(F)a(M)c(F)c(F)u(F) gu(F)a(M)u(F)u(F)a(M)a(M)a(F)a(F)c(F) c(F)c(F)-idT | 57 |
| 57(6) | Chol-g(M)g(M)g(M)au(F)a(M)aa(M)a(M)a (M)u(F)a(M)g(M)a(M)g(M)Tu(F)u(F)g(M)a (M)Ta(M)sa(M)a(M)c(F)a(M)c(F)c(F)u(F) gu(F)a(M)u(F)u(F)a(M)a(M)a(F)a(F)c(F) c(F)c(F)-idT | 57 |

TABLE 2-continued

| aptamer ID | prepared aptamer | SEQ ID NO: |
|---|---|---|
| 57(7) | Chol-g(M)g(M)g(M)au(F)a(M)aa(M)a(M)a (M)u(F)a(M)g(M)a(M)g(M)Tu(F)u(F)g(M)a (M)Ta(M)a(M)sa(M)c(F)a(M)c(F)c(F)u(F) gu(F)a(M)u(F)u(F)a(M)a(M)a(F)a(F)c(F) c(F)c(F)-idT | 57 |
| 57(8) | Chol-g(M)g(M)g(M)au(F)a(M)aa(M)a(M)a (M)u(F)a(M)g(M)a(M)g(M)Tu(F)u(F)g(M)a (M)Ta(M)a(M)a(M)sc(F)a(M)c(F)c(F)u(F) gu(F)a(M)u(F)u(F)a(M)a(M)a(F)a(F)c(F) c(F)c(F)-idT | 57 |
| 57(9) | Chol-g(M)g(M)g(M)au(F)a(M)aa(M)a(M)a (M)u(F)a(M)g(M)a(M)g(M)Tu(F)u(F)g(M)a (M)Ta(M)a(M)a(M)c(F)a(M)c(F)c(F)u(F)s gu(F)a(M)u(F)u(F)a(M)a(M)a(F)a(F)c(F) c(F)c(F)-idT | 57 |
| 58 | Chol-g(M)g(M)g(M)au(F)a(M)aa(M)a(M)a (M)u(F)a(M)g(M)a(M)g(M)u(F)u(F)u(F)g (M)a(M)Ta(M)a(M)a(M)c(F)a(M)c(F)c(F)u (F)gu(F)a(M)u(F)Ta(M)a(M)a(F)a(F)c(F) c(F)c(F)-idT | 58 |
| 59 | Chol-g(M)g(M)g(M)au(F)a(M)aa(M)a(M)a (M)u(F)a(M)g(M)a(M)g(M)u(F)u(F)u(F)g (M)a(M)Ta(M)a(M)c(F)a(M)c(F)c(F)u (F)gu(F)a(M)u(F)u(F)a(M)a(M)a(F)a(F)c (F)c(F)C-idT | 59 |
| 60 | Chol-g(M)g(M)g(M)au(F)a(M)aa(M)a(M)a (M)u(F)a(M)g(M)a(M)g(M)Tu(F)u(F)g(M)a (M)Ta(M)u(F)a(M)c(F)a(M)c(F)c(F)u(F)g u(F)a(M)u(F)u(F)a(M)a(M)a(F)a(F)c(F)c (F)c(F)-idT | 60 |
| 61 | Chol-g(M)g(M)g(M)au(F)a(M)aa(M)a(M)a (M)u(F)a(M)g(M)a(M)g(M)Tu(F)u(F)g(M)a (M)Ta(M)a(M)a(M)c(F)a(M)c(F)c(F)u(F)g u(F)a(M)u(F)u(F)a(M)a(M)aa(F)c(F)c(F) c(F)-idT | 61 |
| 62 | Chol-g(M)g(M)g(M)au(F)a(M)aa(M)a(M)a (M)u(F)a(M)g(M)a(M)g(M)Tu(F)u(F)g(M)a (M)Ta(M)a(M)a(M)c(F)a(M)c(F)c(F)u(F)g u(F)a(M)u(F)u(F)a(M)a(M)a(F)ac(F)c(F) c(F)-idT | 62 |
| 63 | Chol-g(M)g(M)g(M)au(F)a(M)aa(M)a(M)a (M)u(F)a(M)g(M)a(M)g(M)Tu(F)u(F)g(M)a (M)Ta(M)a(M)a(M)c(F)a(M)c(F)c(F)u(F)g u(F)a(M)u(F)u(F)a(M)a(M)aac(F)c(F)c (F)-idT | 63 |

Example 2

RNA Aptamer Bound to NGF

The binding activity of the aptamers represented by aptamer IDs: 1-63 prepared in Example 1 (excluding aptamer IDs: 26(16), (17), (64)-(72), which are PEGylated aptamers) to NGF was evaluated by a surface plasmon resonance method.

As the measuring apparatus, BIAcore2000 manufactured by BIAcore was used and, as the sensor chip, CM5 that reacts with an amino group was used. Human NGF was dissolved in immobilization solution (10 mM sodium acetate, pH 6) at 25-40 µg/ml. For the reaction of an amino group on the protein side and a carboxyl group on the chip side, ethyl-3-carbodiimide hydrochloride and N-hydroxysuccinimide were used. After the reaction, blocking by ethanolamine-HCl was performed. The immobilized amount of NGF was set to 3,000-4,000 RU. An aptamer for analyte was prepared to 0.15 µM-0.5 µM. As a running buffer, solution A was used. Here, solution A is a mixed solution of 145 mM sodium chloride, 5.4 mM potassium chloride, 1.8 mM calcium chloride, 0.8 mM magnesium chloride, 20 mM Tris (pH 7.6), 0.05% Tween 20. As a regeneration solution, a mixed solution of 1M NaCl and 50 mM NaOH was used. NGF was immobilized on FC2, and the results of FC1 were subtracted to give a final sensorgram.

As a result of the measurement, it was found that all the aptamers represented by aptamer IDs: 1-63 (excluding aptamer IDs: 26(16), 26(17), 26(64)-26(72), which are PEGylated aptamers) significantly bind to NGF. As one example thereof, the binding of aptamers represented by aptamer IDs: 26, 48, 57 and NGF is shown in FIG. 1. The aptamer represented by aptamer ID: 26(-) is the aptamer represented by the aptamer ID: 26, wherein the 19th g is modified with O-methyl. This g is that in the consensus sequence shown below, and it is known that modification of said g markedly decreases the physiological activity. The above has shown that the aptamers represented by aptamer IDs: 1-63 specifically bind to NGF.

Whether the aptamers shown by aptamer ID NOs: 1-8, 26(2), 31-38, 52-56, 61 and 63 obtained in Example 1 inhibit the binding of NGF and an NGF receptor (TrkA) was determined using the surface plasmon resonance method.

As directed in BIAcore Company's protocol, Protein A (21181, PIERCE) was immobilized on a CM5 sensor chip. About 500 to 700 RU of human Trk A fused with the Fc portion of IgG (175-TK, R&D systems) was immobilized thereon. As the analyte, a mixture of NGF (0.1 µM) and each aptamer (0.2 µM) was injected after being allowed to stand for 30 minutes. If the aptamer inhibits the binding of NGF and TrkA, the signal on the sensorgram is expected to not rise; if the aptamer does not inhibit the binding, a triple complex will be formed and the signal is expected to rise. When NGF binds stronger to a receptor than an aptamer, the aptamer may be removed and NGF may bind to the receptor. Before starting the inhibition experiment, binding of TrkA and NGF was confirmed. Using the binding amount of NGF and NGF receptor without an aptamer as 100, the binding amount of NGF and NGF receptor added with an aptamer was determined as a correction value. Here, the binding amount is the RU value at the peak top of the sensorgram of BIAcore (RU value immediately after completion of NGF injection). The correction value was subtracted from 100 to give an inhibitory activity %, where not less than 90% shows the presence of inhibitory activity.

As a result of the experiment, all the aptamers shown by aptamer ID NOs: 1-8, 26(2), 31-38, 52-56, 61 and 63 were found to inhibit the binding of NGF and TrkA. A similar experiment was performed for another receptor P75 (p75-Fc; R&D systems). As a result, all the aptamers shown by aptamer ID NOs: 26(2), 56, 61 and 63 obtained in Example 1 were found to inhibit the binding of NGF and P75 by not less than 90%.

Example 3

Neurite Outgrowth Inhibitory Activity of Aptamer

The neurite outgrowth inhibitory activity of the aptamer obtained in Example 1 was evaluated by using Neuroscreen-1 cell, which is a subclone of PC-12 cells.

The cells (2500 cells per well) were cultured for one day in an RPMI-1640 medium containing 2.5% horse serum and 1.25% fetal bovine serum in a 96 well flat-bottom plate coated with collagen type IV. A mixed solution of human NGF (final concentration 1.1 nM or 0.38 nM) and an aptamer (final concentration 500-0.01 nM), which had been prereacted in a serum-free RPMI-1640 medium at room temperature or 37° C. for 30 min to 1 hr, was added. Two days later, the cytoplasm and nuclei were stained using Cellomics Neurite Outgrowth Kit (manufactured by Thermo Scientific), and neurite length per cell was measured by Cellomics ArrayScan VTI (manufactured by Thermo Scientific). With the neurite length per cell obtained by the addition of NGF alone as inhibitory activity 0%, and that of the cell obtained by NGF free culture for 2 days as inhibitory activity 100%, the inhibitory activity of the aptamer was calculated from the neurite length per cell obtained by culturing with the addition of NGF and the aptamer in mixture. When the inhibitory activity was 0% or below, '0%' is indicated. The 50% inhibitory concentration (IC50) was determined from the concentrations at two, above and below points sandwiching the 50% inhibitory activity. The results of the experiment are shown in Table 3-1-3-3.

In Tables 3-1-3-4, IC50 value indicated as "<X" means that the inhibitory activity was not less than 50% when the indicated concentration X was minimum measured concentration. An IC50 value indicated as ">X" means that the inhibitory activity was not more than 50% when the indicated concentration X was the maximum measured concentration. The value shown by * means NGF concentration of 0.38 nM, and others are when the NGF concentration was 1.1 nM. The numerical values in the parentheses are IC50 values described in PCT/JP09/066,457.

As a result, it was found that many of the obtained aptamers have high activity of IC50 of 10 nM or below, including aptamers showing IC50 of 1 nM or below and aptamers showing IC50 of 0.3 nM or below. Particularly, aptamers of aptamer ID: 26(18) ff. showed IC50 value of not more than 0.3 nM.

TABLE 3-1

| aptamer ID | length (mer) | Neurite Outgrowth Assay IC50 (nM) |
|---|---|---|
| 1 | 64 | 2.1 |
| 2 | 69 | <3.0 |
| 3 | 73 | <3.0 |
| 4 | 73 | <3.0 |
| 5 | 61 | <3.0 |
| 6 | 62 | <3.0 |
| 7 | 61 | <3.0 |
| 8 | 62 | <3.0 |
| 9 | 57 | <3.0 |
| 10 | 58 | <3.0 |
| 11 | 57 | 1.5 |
| 12 | 57 | 1.4 |
| 13 | 56 | 1.3 |
| 14 | 57 | 1.2 |
| 15 | 56 | 1.9 |
| 16 | 56 | 1.1 |
| 17 | 54 | <1.0 |
| 18 | 53 | <10 |
| 19 | 52 | 1.3 |
| 20 | 51 | 1.0 |
| 21 | 51 | 1.1 |
| 22 | 49 | 1.3 |
| 23 | 50 | <1.0 |
| 24 | 49 | <1.0 |
| 25 | 47 | <1.0 |
| 26 | 45 | <1.0 |
| 26(1) | 45 | 0.06* |
| 26(2) | 45 | 0.06* |
| 26(3) | 45 | <1.0 |
| 26(4) | 45 | <1.0 |
| 26(5) | 45 | <1.0 |

TABLE 3-1-continued

| aptamer ID | length (mer) | Neurite Outgrowth Assay IC50 (nM) |
|---|---|---|
| 26(6) | 45 | <1.0 |
| 26(7) | 45 | <1.0 |
| 26(8) | 45 | <1.0 |
| 26(9) | 45 | 0.052* |
| 26(10) | 45 | 0.047* |
| 26(11) | 45 | 0.087* |
| 26(12) | 45 | 0.036* |
| 26(13) | 45 | 0.039* |
| 26(14) | 45 | 0.082* |
| 26(15) | 45 | 0.067* |
| 26(16) | 45 | <0.1* |
| 26(17) | 45 | <0.1* |

TABLE 3-2

| aptamer ID | length (mer) | Neurite Outgrowth Assay IC50 (nM) |
|---|---|---|
| 26(18) | 45 | 0.084* |
| 26(19) | 45 | <0.01* |
| 26(20) | 45 | 0.016* |
| 26(21) | 45 | 0.283* |
| 26(22) | 45 | 0.293* |
| 26(23) | 45 | 0.229* |
| 26(24) | 45 | 0.226* |
| 26(25) | 45 | 0.29* |
| 26(26) | 45 | 0.285* |
| 26(27) | 45 | 0.150* |
| 26(28) | 45 | 0.200* |
| 26(29) | 45 | 0.138* |
| 26(30) | 45 | 0.289* |
| 26(31) | 45 | 0.300* |
| 26(32) | 45 | 0.220* |
| 26(33) | 45 | 0.294* |
| 26(34) | 45 | 0.247* |
| 26(35) | 45 | 0.166* |
| 26(36) | 45 | 0.211* |
| 26(37) | 45 | 0.181* |
| 26(38) | 45 | 0.145* |
| 26(39) | 45 | 0.168* |
| 26(40) | 45 | 0.247* |
| 26(41) | 45 | 0.104* |
| 26(42) | 45 | 0.083* |
| 26(43) | 45 | 0.073* |
| 26(44) | 45 | 0.074* |
| 26(45) | 45 | 0.238* |
| 26(46) | 45 | 0.097* |
| 26(47) | 45 | 0.065* |
| 26(48) | 45 | 0.053* |
| 26(49) | 45 | 0.059* |
| 26(50) | 45 | 0.046* |
| 26(51) | 45 | 0.191* |
| 26(52) | 45 | 0.101* |
| 26(53) | 45 | 0.128* |
| 26(54) | 45 | 0.097* |
| 26(55) | 45 | 0.087* |
| 26(56) | 45 | 0.154* |
| 26(57) | 45 | 0.213* |
| 26(58) | 45 | 0.143* |
| 26(59) | 45 | 0.170* |

TABLE 3-3

| aptamer ID | length (mer) | Neurite Outgrowth Assay IC50 (nM) |
|---|---|---|
| 26(60) | 45 | 0.105* |
| 26(61) | 45 | 0.112* |
| 26(62) | 45 | 0.228* |
| 26(63) | 45 | 0.139* |
| 26(64) | 45 | 0.102* |
| 26(65) | 45 | 0.091* |
| 26(66) | 45 | 0.252* |
| 26(67) | 45 | 0.153* |
| 26(68) | 45 | 0.128* |
| 26(69) | 45 | 0.157* |
| 26(70) | 45 | 0.126* |
| 26(71) | 45 | 0.279* |
| 26(72) | 45 | 0.219* |
| 27 | 46 | <1.0 |
| 28 | 44 | <1.0 |
| 29 | 44 | <0.3* |
| 29(1) | 44 | 0.058* |
| 30 | 43 | <0.3* |
| 31 | 69 | <3.0 |
| 32 | 64 | 1.0 |
| 33 | 72 | <3.0 |
| 34 | 62 | <3.0 |
| 35 | 62 | <3.0 |
| 36 | 62 | <3.0 |
| 37 | 61 | <3.0 |
| 38 | 63 | <3.0 |
| 39 | 61 | <3.0 |
| 40 | 60 | <3.0 |
| 41 | 61 | <3.0 |
| 42 | 60 | <3.0 |
| 43 | 58 | <3.0 |
| 44 | 59 | <3.0 |
| 45 | 59 | <3.0 |
| 46 | 57 | 2.6 |
| 47 | 57 | 2.5 |
| 48 | 56 | 1.8 |
| 49 | 57 | 1.8 |
| 50 | 55 | 2.6 |
| 51 | 54 | 2.7 |
| 52 | 57 | 5.9 |
| 53 | 56 | 4.7 |
| 54 | 58 | 3.0 |

TABLE 3-4

| aptamer ID or SEQ ID NO: | length (mer) | Neurite Outgrowth Assay IC50 (nM) |
|---|---|---|
| 55 | 41 | 9.8 |
| 56 | 41 | 4.1 |
| 57 | 41 | <3.0 |
| 57(1) | 41 | <3.0 |
| 57(2) | 41 | <3.0 |
| 57(3) | 41 | <3.0 |
| 57(4) | 41 | <3.0 |
| 57(5) | 41 | <3.0 |
| 57(6) | 41 | <3.0 |
| 57(7) | 41 | <3.0 |
| 57(8) | 41 | <3.0 |
| 57(9) | 41 | <3.0 |
| 58 | 41 | 5.4 |
| 59 | 41 | 6.9 |
| 60 | 41 | <3.0 |
| 61 | 41 | <3.0 |
| 62 | 41 | 4.6 |
| 63 | 41 | <3.0 |
| PCT/JP09/066457, SEQ ID NO: 62 | 74 | 1.9(2.0) |
| PCT/JP09/066457, SEQ ID NO: 67 | 74 | 2.8(2.7) |
| PCT/JP09/066457, SEQ ID NO: 30 | 41 | 44.8(57.6) |

Example 4

Cell Proliferation Inhibitory Activity of Aptamer (TF-1 assay)

The inhibitory activity of the aptamer obtained in Example 1 was evaluated by a growth inhibition assay using TF-1 cells.

Two NGF receptor (human TrkA and human p75) genes were introduced into TF-1 cells (ATCC Number:CRL-2003), which is a human erythroleukemic cell line, by using a retrovirus vector to give cells that highly express two receptors simultaneously and stably. The cells were suspended in an RPMI-1640 medium containing 20% fetal bovine serum, and seeded in a white 96 well flat-bottom plate at 1000 cells (50 µL) per well. Thereto was added a mixed solution 50 µL of human NGF (final concentration 0.076 nM) and the aptamer (final concentration 30-0.01 nM), which had been pre-reacted at room temperature for 30 min in a serum-free RPMI-1640 medium, 3 days later, 100 µL of CellTiter-Glo reagent for CellTiter-Glo Luminescent Cell Viability Assay (manufactured by Promega) was added to each well, chemiluminescence was measured by a microplate reader and the growth of TF-1 cells by NGF stimulation was evaluated. With the amount of luminescence per well obtained by the addition of NGF alone and culture of the cells for 3 days as inhibitory activity 0%, and that of the cell obtained by NGF free culture for 3 days as inhibitory activity 100%, the inhibitory activity of the aptamer was calculated from the amount of luminescence per well obtained by culturing with the addition of NGF and the aptamer in mixture. When the inhibitory activity was 0% or below, '0%' is indicated. The 50% inhibitory concentration (IC50) was determined from the concentrations at two, above and below points sandwiching the 50% inhibitory activity. The results are shown in Table 4-1-4-3.

IC50 value indicated as "<X" means that the inhibitory activity was not less than 50% when the indicated concentration X was minimum measured concentration. IC50 value indicated as ">X" means that the inhibitory activity was not more than 50% when the indicated concentration X was the maximum measured concentration. As a result, it was found that many of the obtained aptamers have high activity of IC50 of 10 nM or below, including aptamers showing IC50 of 1 nM or below and aptamers showing IC50 of 0.3 nM or below. Particularly, of the aptamers shown by aptamer IDs: 26(18) ff., those other than the aptamer of aptamer IDs: 26(36), 26(37), 26(40) show IC50 value of not more than 0.3 nM in a cell proliferation inhibition experiment, indicating that these aptamers have a high inhibitory activity against NGF.

TABLE 4-1

| aptamer ID | length (mer) | TF-1 Assay IC50 (nM) |
| --- | --- | --- |
| 1 | 64 | 20.4 |
| 10 | 58 | 11.1 |
| 19 | 52 | 3.2 |
| 20 | 51 | <1.0 |
| 21 | 51 | 1.0 |
| 22 | 49 | 5.7 |
| 23 | 50 | <1.0 |
| 24 | 49 | <1.0 |
| 25 | 47 | <1.0 |
| 26 | 45 | <1.0 |
| 26(1) | 45 | 0.1 |
| 26(2) | 45 | 0.07 |
| 26(3) | 45 | 4.3 |
| 26(4) | 45 | 6.8 |
| 26(5) | 45 | 3.4 |
| 26(6) | 45 | <1.0 |
| 26(7) | 45 | 2.4 |

TABLE 4-1-continued

| aptamer ID | length (mer) | TF-1 Assay IC50 (nM) |
| --- | --- | --- |
| 26(8) | 45 | >10 |
| 26(9) | 45 | 0.041 |
| 26(10) | 45 | 0.044 |
| 26(11) | 45 | 0.058 |
| 26(12) | 45 | 0.052 |
| 26(13) | 45 | 0.074 |
| 26(14) | 45 | 0.09 |
| 26(15) | 45 | 0.081 |
| 26(16) | 45 | <0.1 |
| 26(17) | 45 | <0.1 |
| 26(18) | 45 | 0.105 |
| 26(19) | 45 | 0.104 |
| 26(20) | 45 | 0.110 |
| 26(21) | 45 | 0.175 |
| 26(22) | 45 | 0.186 |
| 26(23) | 45 | 0.159 |
| 26(24) | 45 | 0.156 |
| 26(25) | 45 | 0.203 |
| 26(26) | 45 | 0.177 |
| 26(27) | 45 | 0.158 |
| 26(28) | 45 | 0.184 |
| 26(29) | 45 | 0.131 |
| 26(30) | 45 | 0.165 |
| 26(31) | 45 | 0.211 |

TABLE 4-2

| aptamer ID | length (mer) | TF-1 Assay IC50 (nM) |
| --- | --- | --- |
| 26(32) | 45 | 0.193 |
| 26(33) | 45 | 0.176 |
| 26(34) | 45 | 0.239 |
| 26(35) | 45 | 0.164 |
| 26(36) | 45 | >0.3 |
| 26(37) | 45 | >0.3 |
| 26(38) | 45 | <0.1 |
| 26(39) | 45 | 0.218 |
| 26(40) | 45 | >0.3 |
| 26(41) | 45 | 0.100 |
| 26(42) | 45 | 0.073 |
| 26(43) | 45 | 0.128 |
| 26(44) | 45 | 0.061 |
| 26(45) | 45 | 0.146 |
| 26(46) | 45 | 0.100 |
| 26(47) | 45 | 0.074 |
| 26(48) | 45 | 0.069 |
| 26(49) | 45 | 0.062 |
| 26(50) | 45 | 0.083 |
| 26(51) | 45 | 0.108 |
| 26(52) | 45 | 0.072 |
| 26(53) | 45 | 0.078 |
| 26(54) | 45 | 0.065 |
| 26(55) | 45 | 0.075 |
| 26(56) | 45 | 0.122 |
| 26(57) | 45 | 0.130 |
| 26(58) | 45 | 0.107 |
| 26(59) | 45 | 0.101 |
| 26(60) | 45 | 0.055 |
| 26(61) | 45 | 0.078 |
| 26(62) | 45 | 0.120 |
| 26(63) | 45 | 0.119 |
| 26(64) | 45 | 0.051 |
| 26(65) | 45 | 0.064 |
| 26(66) | 45 | 0.520 |
| 26(67) | 45 | 0.285 |
| 26(68) | 45 | 0.348 |
| 26(69) | 45 | 0.348 |
| 26(70) | 45 | 0.319 |
| 26(71) | 45 | 0.065 |
| 26(72) | 45 | 0.075 |

TABLE 4-3

| aptamer ID or SEQ ID NO | length (mer) | TF-1 Assay IC50 (nM) |
|---|---|---|
| 27 | 46 | 3.2 |
| 28 | 44 | 1.4 |
| 29 | 44 | 1.0 |
| 29(1) | 44 | 0.154 |
| 30 | 43 | 2.8 |
| 32 | 64 | >30 |
| 43 | 58 | >30 |
| 55 | 41 | 8.0 |
| 57(1) | 41 | 1.2 |
| 57(2) | 41 | 6.2 |
| 57(3) | 41 | 1.5 |
| 57(4) | 41 | 4.2 |
| 57(5) | 41 | 1.7 |
| 57(6) | 41 | 5.3 |
| 57(7) | 41 | 5.3 |
| 57(8) | 41 | 6.2 |
| 57(9) | 41 | 7.0 |
| 60 | 41 | 5.4 |
| 61 | 41 | 1.3 |
| 62 | 41 | 6.3 |
| 63 | 41 | 2.1 |
| PCT/JP09/066457, SEQ ID NO: 62 | 74 | 6.1 |
| PCT/JP09/066457, SEQ ID NO: 67 | 74 | 14.9 |

Example 5

Comparison with NGF Aptamer Described in Prior Art Reference

The binding activity and neurite outgrowth inhibitory activity of the NGF aptamer described in prior art reference (Binkley J et al., (1995) Nucleic Acids Res. 23, 3198) were compared.

The aptamers described in the prior art reference were all unmodified RNAs, and the sequences thereof do not match with the sequences described in the present specification. H1, L2 and L6 showing high binding activity were selected and the aptamers described in the prior art reference were produced by transcription using T7 polymerase. The binding activity was evaluated by a method similar to that in Example 2. With the value obtained by dividing the maximum RU value when the aptamer represented by SEQ ID NO: 57 is bound to NGF by the molecular weight as 100%, when it was not less than 80%, "++" was marked, when it was not less than 50%, "+" was marked, when it was not more than 50%, "−" was marked. In consideration of the difference in the molecular weight of the aptamer, the obtained RU value was amended by dividing by the molecular weight. The neurite outgrowth inhibitory activity was evaluated by a method similar to Example 3. The results are shown in Table 5.

As a result of the experiment, L2 and L6 did not show remarkable binding. When L2 or L6 was immobilized, binding to NGF was observed. Thus, immobilization of NGF is considered to have decreased the affinity of L2 and L6 for NGF. As for the neurite outgrowth inhibitory activity, the aptamer of the present invention shows high neurite outgrowth inhibitory activity, whereas H1, L2, L6 were found to not inhibit the neurite outgrowth even at 500 nM.

TABLE 5

| aptamer ID or aptamer described in document | binding activity | Neurite Outgrowth Assay IC50 (nM) |
|---|---|---|
| 26(10) | ++ | 0.047* |
| 57 | ++ | <3 |
| H1 | + | >500 |
| L2 | − | >500 |
| L6 | − | >500 |

Example 6

Comparison with NGF Aptamer Described in WO02/077262

The binding activity, neurite outgrowth inhibitory activity, and cell proliferation inhibitory activity of the NGF aptamer described in WO02/077262 were measured, and compared with those of the aptamer represented by aptamer ID: 26(19) specified in the present invention. As NGF aptamer described in WO02/077262, Seq ID Nos. 38 and 42 were selected. The sequences of these aptamers are as follows, and produced by the phosphoramidite method shown in Example 1. Here, brominated dU was used as N(N=5−Br−dU(5-bromo-2'-deoxyuridine)).

Seq ID No. 70
ANANANANGGGAGGACGANGCGGGCA-
CACNNAAANCCACNNCACCNNACAANNCCNNNANCNGC

AGACGACGAGCGGGAAAAAAAA

Seq ID No. 71
ANANANANGGGAGGACGANGCGGGC-
CCCAAACACNNGNNCCNANCNNNCAACCCCCCNNGANCC

AGACGACGAGCGGGAAAAAAAA

The binding activity was evaluated by a method similar to that in Example 2 and using a surface plasmon resonance method. With the value obtained by dividing the maximum RU value when the aptamer represented by aptamer ID: 26(19) is bound to NGF by the molecular weight as 100%, when it was not less than 80%, "++" was marked, when it was 79-51%, "+" was marked, when it was not more than 50%, "−" was marked. In consideration of the difference in the molecular weight of the aptamer, the obtained RU value was amended by dividing by the molecular weight. The neurite outgrowth inhibitory activity and cell proliferation inhibitory activity were evaluated by a method similar to Examples 3 and 4. The results are shown in Table 6.

As a result of the experiment, the binding activity of the NGF aptamer described in WO02/077262 was found to be extremely low as compared to the aptamer of the present invention. As for the neurite outgrowth inhibitory activity and the cell proliferation inhibitory activity, the aptamer of the present invention showed high inhibitory activity, whereas the aptamer described in WO02/077262 did not show an inhibitory activity at all.

TABLE 6

| aptamer | binding activity | Neurite Outgrowth Assay IC50 (nM) | TF-1 Assay IC50 (nM) |
|---|---|---|---|
| aptamer ID: 26 (19) | ++ | <0.01 | 0.104 |
| WO02/077262, Seq ID No. 38 | − | >200 | >200 |
| WO02/077262, Seq ID No. 42 | − | >200 | >200 |

Example 7

Cross-Reactivity with Other Neurotrophin

Neurotrophin is a generic term of the NGF-related gene family, and other BDNF (brain-derived neurotrophic factor), NT-3 (neurotrophin-3) and NT-4/5 (neurotrophin-4/5) are known. As neurotrophin receptor, low-affinity receptor p75 and high-affinity receptor Trk have been identified. Trk also forms a family which includes 3 kinds of TrkA which is an NGF receptor, TrkB which is a receptor of BDNF and NT-4/5, and TrkC which is an NT-3 receptor. The aptamer specified in the present invention has high binding activity to and inhibitory activity against NGF. The activity on other neurotrophins was examined.

The binding of the aptamer represented by aptamer ID: 26(2) and human BDNF (manufactured by R&D systems), human NT-3 (manufactured by R&D systems), human NT-4/5 (manufactured by R&D systems) was evaluated by the surface plasmon resonance method in the same manner as in Example 2.

As a result, the binding to NT-3 was not observed. It was clarified that the dissociation rate was very fast for BDNF and NT-4/5, and the binding activity was clearly lower than that to NGF.

The physiological inhibitory activity of the aptamers represented by aptamer IDs: 26(2), 52, 63-65 against BDNF, NT-3, NT-4/5 was evaluated by a growth inhibition assay using TF-1 cells.

Human receptor genes (TrkB, TrkC, p75) for respective neurotrophic factors were introduced into TF-1 cells (ATCC Number:CRL-2003), which is a human erythroleukemic cell line, by using a retrovirus vector to give cells that highly express these receptors stably. TF-1 cells introduced with TrkB and p75 were used for the evaluation of inhibitory activity against BDNF, TF-1 cells introduced with TrkC and p75 were used for the evaluation against NT-3, and TF-1 cells introduced with TrkB alone were used for the evaluation against NT-4/5. These cells were suspended in an RPMI-1640 medium containing 20% fetal bovine serum, and seeded in a white 96 well flat-bottom plate at 1000 cells (50 µL) per well. Thereto was added a mixed solution 50 µL of human BDNF (final concentration 0.074 nM) or NT-3 (final concentration 0.074 nM) or NT-4/5 (final concentration 0.071 nM) and the aptamer (final concentration 30-0.01 nM), which had been pre-reacted at room temperature for 30 min in a serum-free RPMI-1640 medium, 3 days later, 100 µL of CellTiter-Glo reagent for CellTiter-Glo Luminescent Cell Viability Assay (manufactured by Promega) was added to each well, chemiluminescence was measured by a microplate reader. With the amount of luminescence per well obtained by the addition of BDNF or NT-3 or NT-4/5 alone and culture of the cells for 3 days as inhibitory activity 0%, and that of the cell obtained by culture for 3 days without addition of BDNF or NT3 or NT-4/5 as inhibitory activity 100%, the inhibitory activity of the aptamer was calculated from the amount of luminescence per well obtained by culturing with the addition of BDNF or NT3 or NT-4/5 and the aptamer in mixture. When the inhibitory activity was 0% or below, '0%' is indicated. The 50% inhibitory concentration (IC50) was determined from the concentrations at two, above and below points sandwiching the 50% inhibitory activity. The results are shown in Table 7.

An IC50 value indicated as ">X" means that the inhibitory activity was not more than 50% when the indicated concentration X was the maximum measured concentration. All aptamers measured showed IC50 of not less than 1000 nM for BDNF and NT-3. In addition, IC50 was not less than 300 nM for NT-4/5. From the above results, these aptamers were found to have specifically inhibited NGF.

TABLE 7

| aptamer ID | BDNF (IC50) | NT-3 (IC50) | NT-4/5 (IC50) | NGF (IC50) |
|---|---|---|---|---|
| 26(2) | >1000 nM | >1000 nM | >300 nM | 0.07 nM |
| 26(52) | >1000 nM | >1000 nM | >300 nM | 0.072 nM |
| 26(63) | >1000 nM | >1000 nM | >300 nM | 0.119 nM |
| 26(64) | >1000 nM | >1000 nM | >300 nM | 0.051 nM |
| 26(65) | >1000 nM | >1000 nM | >300 nM | 0.064 nM |

Example 8

Analgesic Action by NGF Aptamer

To study the analgesic action of NGF aptamer on NGF-induced pain, a thermal hyperalgesia model induced by subcutaneous administration of NGF to rat hind paw was used. For the experiment, Jcl:SD rats (6-week-old) were used. As an index of thermal hyperalgesia, response latency of escape behavior to infrared irradiation from a plantar heat stimulation measuring apparatus (manufactured by Ugo Basile) to the planta was used. On the previous day of the test, acclimation to the evaluation system was performed. Before administration on the day of the test, escape response latency was measured, and animals that showed not less than 10 sec and less than 20 sec were used. Recombinant human beta-NGF (R&D Systems, final concentration 50 µg/ml) and a test substance were mixed with vehicle (20 mM Tris-HCl (pH 7.6), 145 mM NaCl, 5.4 mM KCl, 0.8 mM $MgCl_2$, 1.8 mM $CaCl_2$, 0.1% BSA), incubated at room temperature for 30 min, and subcutaneously administered to the left hind sole at 10 µl. The escape response latency was measured 3 hr later and 5 hr later. The anti-NGF aptamer represented by aptamer ID: 26(2) was administered at a final concentration of 0.5, 5, 10 mg/ml (molar ratio relative to NGF about: 10, 100, 200-fold). As a control, vehicle or a mixture of vehicle and NGF was administered in the same manner. The results are shown in Table 8 (Mean±SEM, Vehicle group and NGF group: n=12, SEQ ID NO: 26(2) administration group: n=9).

At 3 hr and 5 hr after administration, the NGF group showed significantly low escape response latency as compared to the vehicle group. At 3 hr after administration, the escape response latency of the aptamer ID: 26(2) administration group was significantly high (p<0.05) at 5, 10 mg/ml as compared to the NGF alone administration group, and at 5 hr after administration, the escape response latency of the aptamer ID: 26(2) administration group was high (p<0.01) at 0.5, 5, 10 mg/ml as compared to the NGF alone administration group. This has revealed that an anti-NGF aptamer has an analgesic action on NGF-induced pain.

TABLE 8

| treated group | escape response latency (sec) | | |
| --- | --- | --- | --- |
| | before treatment | 3 hr later | 5 hr later |
| vehicle | 13.58 ± 0.64 | 12.01 ± 1.64 | 12.26 ± 0.66 |
| NGF | 13.55 ± 0.51 | 9.88 ± 0.77 | 8.59 ± 0.47 |
| NGF-0.5 mg/ml aptamer ID: 26(2) | 13.78 ± 0.73 | 11.49 ± 0.76 | 12.79 ± 0.75 |
| NGF-5 mg/ml aptamer ID: 26(2) | 13.21 ± 0.62 | 12.72 ± 0.71 | 12.19 ± 0.35 |
| NGF-10 mg/ml aptamer ID: 26(2) | 14.49 ± 0.82 | 12.92 ± 1.71 | 12.96 ± 0.64 |

Example 9

Analgesic Action of NGF Aptamer on Postoperative Pain Model

To study the efficacy of NGF aptamer therapy, a postoperative pain model which was to have induced thermal hyperalgesia was used. For the experiment, Crl:CD(SD) rats (5-week-old) were used. The tip of a catheter was indwelled in the femoral vein, the other tip was exposed from the back of the rat. One week later, Quick connect infusion system (manufactured by Strategic applications incorporated) was set on the rat, thermal hyperalgesia was evaluated one week later. As an index of thermal hyperalgesia, response latency of escape behavior to infrared irradiation from a plantar heat stimulation measuring apparatus (manufactured by Ugo Basile) to the planta was used. Acclimation to the evaluation system was performed 3 days before the start of the test. On the day of the test, escape response latency was measured, and animals that showed not less than 10 sec and less than 20 sec were used. The anti-NGF aptamer represented by aptamer ID: 26(66) was dissolved in saline and intravenously administered with a syringe pump (manufactured by TERUMO CORPORATION) at 13.61 mg/240 ml/kg/96 hr in a sustained manner (the mass of the aptamer corresponds to the region free of PEG). As a control, vehicle was administered in the same manner. At 1 hr from the start of the administration, the skin and fascia of the right hind sole were incised, the flexor was vertically bisected, and the skin was sutured. The escape response latency was measured after incision operation, and 1, 2, 3, 4 days thereafter. The results are shown in Table 9 (Mean±SEM, n=9).

The vehicle group showed significantly small (p<0.01) escape response latency at 1, 2, 3, 4 days after administration-incision operation as compared to before administration-incision operation. At 1, 2, 3, 4 days after administration-incision operation, the escape response latency of the aptamer (aptamer ID: 26(66)) administration group was significantly high (1, 2, 4 days later: p<0.01, 3 days later: p<0.05) as compared to the vehicle group. This has revealed that an anti-NGF aptamer has an analgesic action on postoperative pain model.

TABLE 9

| after administration- | escape response latency(sec) | |
| --- | --- | --- |
| incision operation | vehicle | aptamer ID: 26(66) |
| day 0 | 13.21 ± 0.51 | 13.36 ± 0.43 |
| day 1 | 4.97 ± 0.6 | 10.02 ± 1.33 |
| day 2 | 6.46 ± 0.71 | 10.24 ± 0.63 |
| day 3 | 6.78 ± 0.52 | 10.74 ± 1.37 |
| day 4 | 7.08 ± 1.32 | 13.01 ± 1.01 |

INDUSTRIAL APPLICABILITY

The aptamer and the complex of the present invention can be useful as medicaments, diagnostic agents or reagents for diseases such as pain, inflammatory disease and the like. The aptamer and the complex of the present invention can also be useful for the purification and concentration of NGF, as well as detection and quantification of NGF.

This application is based on a patent application No. 2010-068546 filed in Japan (filing date: Mar. 24, 2010), the contents of which are incorporated in full herein.

The invention claimed is:

1. An aptamer of 73 nucleotides or fewer, comprising any one of the nucleotide sequences (a), (b) or (c) below:
   (a) a nucleotide sequence shown by SEQ ID NO: 26, wherein uracil may be thymine;
   (b) a nucleotide sequence shown by SEQ ID NO: 26, wherein uracil may be thymine, wherein 1 to 4 nucleotides other than in the sequence UGAAAGAAACC (SEQ ID NO: 67) are substituted, deleted, inserted or added;
   (c) a nucleotide sequence having an identity of 90% or more to the nucleotide sequence of SEQ ID NO: 26, wherein uracil may be thymine, that comprises the sequence UGAAAGAAACC (SEQ ID NO: 67);

wherein the aptamer binds to Nerve Growth Factor (NGF) and inhibits the following (i) and/or (ii):
   (i) binding of NGF to an NGF receptor;
   (ii) neurite outgrowth activity or cell proliferation activity of NGF.

2. The aptamer according to claim 1, wherein at least one nucleotide is modified.

3. The aptamer according to claim 1, wherein the groups at the 2'-position of a ribose of respective pyrimidine nucleotides are the same or different and are hydroxyl or an atom or group selected from the group consisting of a hydrogen atom, a fluorine atom and a methoxy group.

4. The aptamer according to claim 1, wherein the groups at the 2'-position of a ribose of respective purine nucleotides are the same or different and are hydroxyl or an atom or group selected from the group consisting of a hydrogen atom, a fluorine atom and a methoxy group.

5. The aptamer according to claim 1, which inhibits neurite outgrowth activity or cell proliferation activity of NGF.

6. The aptamer according to claim 5, which has a 50% inhibitory concentration of not more than 10 nM.

7. The aptamer according to claim 1, which does not bind to NT-3.

8. A nucleic acid comprising the nucleotide sequence shown by SEQ ID NO: 26 and having a base length of not more than 73.

9. A nucleic acid consisting of the nucleotide sequence shown by SEQ ID NO: 26.

10. The nucleic acid according to claim 8, wherein at least one nucleotide is modified.

11. The nucleic acid according to claim 10, wherein the groups at the 2'-position of a ribose of respective pyrimidine nucleotides are the same or different and are hydroxyl or an atom or group selected from the group consisting of a hydrogen atom, a fluorine atom and a methoxy group.

12. The nucleic acid according to claim 10, wherein the groups at the 2'-position of a ribose of respective purine nucleotides are the same or different and are hydroxyl or an atom or group selected from the group consisting of a hydrogen atom, a fluorine atom and a methoxy group.

13. A complex comprising:
   (a) the aptamer according to claim 1 or a nucleic acid comprising the nucleotide sequence shown by SEQ ID NO: 26 and having a length of not more than 73 nucleotides, and
   (b) a labeling substance, enzyme, drug delivery vehicle or drug, which is combined with the aptamer or the nucleic acid.

14. A pharmaceutical composition comprising:
   an aptamer of 73 nucleotides or fewer, comprising any one of the nucleotide sequences (a), (b) or (c) below:
   (a) a nucleotide sequence shown by SEQ ID NO: 26, wherein uracil may be thymine;
   (b) a nucleotide sequence shown by SEQ ID NO: 26, wherein uracil may be thymine,
      wherein 1 to 4 nucleotides other than in the sequence UGAAAGAAACC (SEQ ID NO: 67) are substituted, deleted, inserted or added;
   (c) a nucleotide sequence having an identity of 90% or more to the nucleotide sequence of SEQ ID NO: 26, wherein uracil may be thymine, that comprises the sequence UGAAAGAAACC (SEQ ID NO: 67);
   wherein the aptamer binds to Nerve Growth Factor (NGF) and inhibits binding of NGF to an NGF receptor; or
   (d) a complex comprising (a) or (b) or (c) above, and a labeling substance, enzyme, drug delivery vehicle or drug, which is combined with the aptamer.

15. An anti-pain medicament comprising:
   an aptamer of 73 nucleotides or fewer, comprising any one of the nucleotide sequences (a), (b) or (c) below:
   (a) a nucleotide sequence shown by SEQ ID NO: 26, wherein uracil may be thymine;
   (b) a nucleotide sequence shown by SEQ ID NO: 26, wherein uracil may be thymine,
      wherein 1 to 4 nucleotides other than in the sequence UGAAAGAAACC (SEQ ID NO: 67) are substituted, deleted, inserted or added;
   (c) a nucleotide sequence having an identity of 90% or more to the nucleotide sequence of SEQ ID NO: 26, wherein uracil may be thymine, that comprises the sequence UGAAAGAAACC (SEQ ID NO: 67);
   wherein the aptamer binds to Nerve Growth Factor (NGF) and inhibits binding of NGF to an NGF receptor; or
   (d) a complex comprising (a) or (b) or (c) above, and an enzyme, drug delivery vehicle or drug, which is combined with the aptamer.

16. A method of treating pain, comprising administering:
   (a) the aptamer according to claim 1,
   (b) a nucleic acid comprising the nucleotide sequence shown by SEQ ID NO: 26 and having a length of not more than 73 nucleotides, or
   (c) a complex comprising (a) or (b) above, and an enzyme, drug delivery vehicle or drug, which is combined with the aptamer or the nucleic acid,
   to a subject in need thereof.

* * * * *

SEQUENCE LISTING

```
<160> NUMBER OF SEQ ID NOS: 72

<210> SEQ ID NO 1
<211> LENGTH: 64
<212> TYPE: RNA
<213> ORGANISM: Artificial
<220> FEATURE:
<223> OTHER INFORMATION: nucleic acid having binding activity against
      NGF

<400> SEQUENCE: 1
gggagaacuu cgaccagaag uuugaaagaa acccaaauua aagugaacag uaugugcgca      60
uaca                                                                  64

<210> SEQ ID NO 2
<211> LENGTH: 69
<212> TYPE: RNA
<213> ORGANISM: Artificial
<220> FEATURE:
```

```
<223> OTHER INFORMATION: nucleic acid having binding activity against
      NGF

<400> SEQUENCE: 2
gggagaacuu cgaccagaag uuugaaagaa acccaaauua aagugaagua ugugcgcaua    60
cauuccuca                                                           69

<210> SEQ ID NO 3
<211> LENGTH: 73
<212> TYPE: RNA
<213> ORGANISM: Artificial
<220> FEATURE:
<223> OTHER INFORMATION: nucleic acid having binding activity against
      NGF

<400> SEQUENCE: 3
gggagaacuu cgaccagaag uuugaaagaa acccaaauua aaggaacagu augugcgcau    60
acauggaucc uca                                                      73

<210> SEQ ID NO 4
<211> LENGTH: 73
<212> TYPE: RNA
<213> ORGANISM: Artificial
<220> FEATURE:
<223> OTHER INFORMATION: nucleic acid having binding activity against
      NGF

<400> SEQUENCE: 4
gggagaacuu cgaccagaag uuugaaagaa acccaaauua aagugaacag uaugugcgca    60
uacuggaucc uca                                                      73

<210> SEQ ID NO 5
<211> LENGTH: 61
<212> TYPE: RNA
<213> ORGANISM: Artificial
<220> FEATURE:
<223> OTHER INFORMATION: nucleic acid having binding activity against
      NGF

<400> SEQUENCE: 5
gggagaacuu cgaccagaag uuugaaagaa acccaaauua aaaacaguau gugcgcauac    60
a                                                                   61

<210> SEQ ID NO 6
<211> LENGTH: 62
<212> TYPE: RNA
<213> ORGANISM: Artificial
<220> FEATURE:
<223> OTHER INFORMATION: nucleic acid having binding activity against
      NGF

<400> SEQUENCE: 6
gggagaacuu cgaccagaag uuugaaagaa acccaaaaaa gugaacagua ugugcgcaua    60
ca                                                                  62

<210> SEQ ID NO 7
<211> LENGTH: 61
<212> TYPE: RNA
<213> ORGANISM: Artificial
<220> FEATURE:
<223> OTHER INFORMATION: nucleic acid having binding activity against
      NGF

<400> SEQUENCE: 7
```

```
gggagaacuu cgaccagaag uuugaaagaa acccaaauua aaggaaguau gugcgcauac    60
a                                                                    61

<210> SEQ ID NO 8
<211> LENGTH: 62
<212> TYPE: RNA
<213> ORGANISM: Artificial
<220> FEATURE:
<223> OTHER INFORMATION: nucleic acid having binding activity against
      NGF

<400> SEQUENCE: 8
gggagaacuu cgaccagaag uuugaaagaa acccaaauua aagugaacag augugcgcau    60
ca                                                                   62

<210> SEQ ID NO 9
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 9
gggagaacuu cgaccagaag uuugaaagaa acccaaauua aaaagaugug cgcauca       57

<210> SEQ ID NO 10
<211> LENGTH: 58
<212> TYPE: RNA
<213> ORGANISM: Artificial
<220> FEATURE:
<223> OTHER INFORMATION: nucleic acid having binding activity against
      NGF

<400> SEQUENCE: 10
gggagaacuu cgccagaagu uugaaagaaa cccaaauuaa aaaguaugug cgcauaca      58

<210> SEQ ID NO 11
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 11
gggagaacuu cgccagaagu uugaaagaaa cccaaauaaa aaguaugugc gcauaca       57

<210> SEQ ID NO 12
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 12
gggagaacuu cgccagaagu uugaaagaaa cccaaauuaa aaguaugugc gcauaca       57

<210> SEQ ID NO 13
<211> LENGTH: 56
<212> TYPE: RNA
<213> ORGANISM: Artificial
<220> FEATURE:
<223> OTHER INFORMATION: nucleic acid having binding activity against
```

NGF

<400> SEQUENCE: 13
gggagaacuu cgccagaagu uugaaagaaa cccaaauuaa aguaugugcg cauaca        56

<210> SEQ ID NO 14
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 14
gggagaacuu cgccagaagu uugaaagaaa cccaauuaaa aaguaugugc gcauaca       57

<210> SEQ ID NO 15
<211> LENGTH: 56
<212> TYPE: RNA
<213> ORGANISM: Artificial
<220> FEATURE:
<223> OTHER INFORMATION: nucleic acid having binding activity against
      NGF

<400> SEQUENCE: 15
gggagaacuu cgccagaagu uugaaagaaa cccauuaaaa aguaugugcg cauaca        56

<210> SEQ ID NO 16
<211> LENGTH: 56
<212> TYPE: RNA
<213> ORGANISM: Artificial
<220> FEATURE:
<223> OTHER INFORMATION: nucleic acid having binding activity against
      NGF

<400> SEQUENCE: 16
gggagaacuu cgccagaagu uugaaagaaa cccaaauuaa aaagaugugc gcauca        56

<210> SEQ ID NO 17
<211> LENGTH: 54
<212> TYPE: RNA
<213> ORGANISM: Artificial
<220> FEATURE:
<223> OTHER INFORMATION: nucleic acid having binding activity against
      NGF

<400> SEQUENCE: 17
gggagaacuu cgccagaagu uugaaagaaa cccaaauuaa agaugugcgc auca          54

<210> SEQ ID NO 18
<211> LENGTH: 53
<212> TYPE: RNA
<213> ORGANISM: Artificial
<220> FEATURE:
<223> OTHER INFORMATION: nucleic acid having binding activity against
      NGF

<400> SEQUENCE: 18
gggagaacuu cgccagaagu uugaaagaaa cccaaauaaa gaugugcgca uca           53

<210> SEQ ID NO 19
<211> LENGTH: 52
<212> TYPE: RNA
<213> ORGANISM: Artificial
<220> FEATURE:
<223> OTHER INFORMATION: nucleic acid having binding activity against
      NGF

<400> SEQUENCE: 19
gggagaacuu cgccagaagu uugaaagaaa cccaaauaaa gaugugcgca uc    52

<210> SEQ ID NO 20
<211> LENGTH: 51
<212> TYPE: RNA
<213> ORGANISM: Artificial
<220> FEATURE:
<223> OTHER INFORMATION: nucleic acid having binding activity against
      NGF

<400> SEQUENCE: 20
gggagaacuu cgccagaagu uugaaagaaa cccaaauaaa gugugcgcac a    51

<210> SEQ ID NO 21
<211> LENGTH: 51
<212> TYPE: RNA
<213> ORGANISM: Artificial
<220> FEATURE:
<223> OTHER INFORMATION: nucleic acid having binding activity against
      NGF

<400> SEQUENCE: 21
gggagaacuu cgccagaagu uugaaagaaa cccaaauaaa gagugcgcuc a    51

<210> SEQ ID NO 22
<211> LENGTH: 49
<212> TYPE: RNA
<213> ORGANISM: Artificial
<220> FEATURE:
<223> OTHER INFORMATION: nucleic acid having binding activity against
      NGF

<400> SEQUENCE: 22
gggagacucg ccagaguuga agaaaccca aauaaagaug ugcgcauca    49

<210> SEQ ID NO 23
<211> LENGTH: 50
<212> TYPE: RNA
<213> ORGANISM: Artificial
<220> FEATURE:
<223> OTHER INFORMATION: nucleic acid having binding activity against
      NGF

<400> SEQUENCE: 23
gggagaacuu cgccagaagu uugaaagaaa cccaaauaag ugugcgcaca    50

<210> SEQ ID NO 24
<211> LENGTH: 49
<212> TYPE: RNA
<213> ORGANISM: Artificial
<220> FEATURE:
<223> OTHER INFORMATION: nucleic acid having binding activity against
      NGF

<400> SEQUENCE: 24
gggagaacuu cgccagaagu uugaaagaaa cccaaauaag ugugcgcac    49

<210> SEQ ID NO 25
<211> LENGTH: 47
<212> TYPE: RNA
<213> ORGANISM: Artificial
<220> FEATURE:
<223> OTHER INFORMATION: nucleic acid having binding activity against
      NGF

<400> SEQUENCE: 25
gggagacucg ccagaguuga agaaaccca aauaaagugu gcgcaca        47

<210> SEQ ID NO 26
<211> LENGTH: 45
<212> TYPE: RNA
<213> ORGANISM: Artificial
<220> FEATURE:
<223> OTHER INFORMATION: nucleic acid having binding activity against
      NGF

<400> SEQUENCE: 26
gggagacucg ccagaguuga agaaaccca aauaagugug cgcac          45

<210> SEQ ID NO 27
<211> LENGTH: 46
<212> TYPE: RNA
<213> ORGANISM: Artificial
<220> FEATURE:
<223> OTHER INFORMATION: nucleic acid having binding activity against
      NGF

<400> SEQUENCE: 27
gggagacucg cagaguugaa agaaacccaa auaaagugug cgcaca        46

<210> SEQ ID NO 28
<211> LENGTH: 44
<212> TYPE: RNA
<213> ORGANISM: Artificial
<220> FEATURE:
<223> OTHER INFORMATION: nucleic acid having binding activity against
      NGF

<400> SEQUENCE: 28
gggagacucg cagaguugaa agaaacccaa auagugugc gcac           44

<210> SEQ ID NO 29
<211> LENGTH: 44
<212> TYPE: RNA
<213> ORGANISM: Artificial
<220> FEATURE:
<223> OTHER INFORMATION: nucleic acid having binding activity against
      NGF

<400> SEQUENCE: 29
gggagacucg ccagaguuga agaaaccca aauagugugc gcac           44

<210> SEQ ID NO 30
<211> LENGTH: 43
<212> TYPE: RNA
<213> ORGANISM: Artificial
<220> FEATURE:
<223> OTHER INFORMATION: nucleic acid having binding activity against
      NGF

<400> SEQUENCE: 30
gggagacucg cagaguugaa agaaacccaa auagugugcg cac           43

<210> SEQ ID NO 31
<211> LENGTH: 69
<212> TYPE: RNA
<213> ORGANISM: Artificial
<220> FEATURE:
<223> OTHER INFORMATION: nucleic acid having binding activity against
      NGF

<400> SEQUENCE: 31

-continued

```
gggagaacuu cgaccagaag ucgauaacga acaaaacucc caaaggaaua uaugugcgca    60
uacauggau                                                           69

<210> SEQ ID NO 32
<211> LENGTH: 64
<212> TYPE: RNA
<213> ORGANISM: Artificial
<220> FEATURE:
<223> OTHER INFORMATION: nucleic acid having binding activity against
      NGF

<400> SEQUENCE: 32
gggagaacuu cgaccagaag ucgauaacga acaaaacucc caaaggaaua uaugugcgca    60
uaca                                                                64

<210> SEQ ID NO 33
<211> LENGTH: 72
<212> TYPE: RNA
<213> ORGANISM: Artificial
<220> FEATURE:
<223> OTHER INFORMATION: nucleic acid having binding activity against
      NGF

<400> SEQUENCE: 33
gggagaacuu cgaccagaag ucgauaacga acaaaacucc caaaggaaua uaugugcgca    60
uacauggauc cu                                                       72

<210> SEQ ID NO 34
<211> LENGTH: 62
<212> TYPE: RNA
<213> ORGANISM: Artificial
<220> FEATURE:
<223> OTHER INFORMATION: nucleic acid having binding activity against
      NGF

<400> SEQUENCE: 34
gggagaacuu cgaccagaag ucgauaacga acaaaacucc caaaggaaua ugugcgcaua    60
ca                                                                  62

<210> SEQ ID NO 35
<211> LENGTH: 62
<212> TYPE: RNA
<213> ORGANISM: Artificial
<220> FEATURE:
<223> OTHER INFORMATION: nucleic acid having binding activity against
      NGF

<400> SEQUENCE: 35
gggagaacuu cgaccagaag ucgauaacga acaaaacucc caaagguaua ugugcgcaua    60
ca                                                                  62

<210> SEQ ID NO 36
<211> LENGTH: 62
<212> TYPE: RNA
<213> ORGANISM: Artificial
<220> FEATURE:
<223> OTHER INFORMATION: nucleic acid having binding activity against
      NGF

<400> SEQUENCE: 36
gggagaacuu cgaccagaag ucgauaacga acaaaacucc caaaaauaua ugugcgcaua    60
ca                                                                  62
```

<210> SEQ ID NO 37
<211> LENGTH: 61
<212> TYPE: RNA
<213> ORGANISM: Artificial
<220> FEATURE:
<223> OTHER INFORMATION: nucleic acid having binding activity against
      NGF

<400> SEQUENCE: 37
gggagaacuu cgaccagaag ucgauaacga acaaaacucc cggaauauau gugcgcauac     60
a                                                                    61

<210> SEQ ID NO 38
<211> LENGTH: 63
<212> TYPE: RNA
<213> ORGANISM: Artificial
<220> FEATURE:
<223> OTHER INFORMATION: nucleic acid having binding activity against
      NGF

<400> SEQUENCE: 38
gggagaacuu cgaccagaag ucgauaacga acaaaacucc caaaggaaua uaugugcgca     60
uac                                                                  63

<210> SEQ ID NO 39
<211> LENGTH: 61
<212> TYPE: RNA
<213> ORGANISM: Artificial
<220> FEATURE:
<223> OTHER INFORMATION: nucleic acid having binding activity against
      NGF

<400> SEQUENCE: 39
gggagaacuu cgaccagaag ucgauaacga acaaaacucc caaaggaaau gugcgcauac     60
a                                                                    61

<210> SEQ ID NO 40
<211> LENGTH: 60
<212> TYPE: RNA
<213> ORGANISM: Artificial
<220> FEATURE:
<223> OTHER INFORMATION: nucleic acid having binding activity against
      NGF

<400> SEQUENCE: 40
gggagaacuu cgaccagaag ucgauaacga acaaaacucc caaauauaug ugcgcauaca     60

<210> SEQ ID NO 41
<211> LENGTH: 61
<212> TYPE: RNA
<213> ORGANISM: Artificial
<220> FEATURE:
<223> OTHER INFORMATION: nucleic acid having binding activity against
      NGF

<400> SEQUENCE: 41
gggagaacuu cgaccagaag ucgauaacga acaaaacucc caaagguaau gugcgcauac     60
a                                                                    61

<210> SEQ ID NO 42
<211> LENGTH: 60
<212> TYPE: RNA
<213> ORGANISM: Artificial

```
<220> FEATURE:
<223> OTHER INFORMATION: nucleic acid having binding activity against
      NGF

<400> SEQUENCE: 42
gggagaacuu cgaccagaag ucgauaacga acaaaacucc cggaauaaug ugcgcauaca    60

<210> SEQ ID NO 43
<211> LENGTH: 58
<212> TYPE: RNA
<213> ORGANISM: Artificial
<220> FEATURE:
<223> OTHER INFORMATION: nucleic acid having binding activity against
      NGF

<400> SEQUENCE: 43
gggagaacuu cgaccagaag ucgauaacga acaaaacucc caaauaugug cgcauaca    58

<210> SEQ ID NO 44
<211> LENGTH: 59
<212> TYPE: RNA
<213> ORGANISM: Artificial
<220> FEATURE:
<223> OTHER INFORMATION: nucleic acid having binding activity against
      NGF

<400> SEQUENCE: 44
gggagaacuu cgaccagaag ucgauaacga acaaaacucc caaaggaugu gcgcauaca    59

<210> SEQ ID NO 45
<211> LENGTH: 59
<212> TYPE: RNA
<213> ORGANISM: Artificial
<220> FEATURE:
<223> OTHER INFORMATION: nucleic acid having binding activity against
      NGF

<400> SEQUENCE: 45
gggagaacuu cgaccagaag ucgauaacga acaaaacucc caaauaaugu gcgcauaca    59

<210> SEQ ID NO 46
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 46
gggagaacuu cgaccagaag ucgauaacga acaaaacucc caaauaugug cgcauac    57

<210> SEQ ID NO 47
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 47
gggagaacuu cgaccagagu cgauaacgaa caaaacuccc aaauaugugc gcauaca    57

<210> SEQ ID NO 48
<211> LENGTH: 56
<212> TYPE: RNA
<213> ORGANISM: Artificial
<220> FEATURE:
```

```
<223> OTHER INFORMATION: nucleic acid having binding activity against
      NGF

<400> SEQUENCE: 48
gggagaacuu cgaccagagu cgauaacgaa caaaacuccc aaauaugugc gcauac        56

<210> SEQ ID NO 49
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 49
gggagaacuu cgaccagaag ucgauaacga acaaaacucc caauaugugc gcauaca      57

<210> SEQ ID NO 50
<211> LENGTH: 55
<212> TYPE: RNA
<213> ORGANISM: Artificial
<220> FEATURE:
<223> OTHER INFORMATION: nucleic acid having binding activity against
      NGF

<400> SEQUENCE: 50
gggagaacuu cgaccagagu cgauaacgaa caaaacuccc aauaugugcg cauac        55

<210> SEQ ID NO 51
<211> LENGTH: 54
<212> TYPE: RNA
<213> ORGANISM: Artificial
<220> FEATURE:
<223> OTHER INFORMATION: nucleic acid having binding activity against
      NGF

<400> SEQUENCE: 51
ggagaacuuc gaccagaguc gauaacgaac aaaacuccaa auaugugcgc auac         54

<210> SEQ ID NO 52
<211> LENGTH: 57
<212> TYPE: RNA
<213> ORGANISM: Artificial
<220> FEATURE:
<223> OTHER INFORMATION: nucleic acid having binding activity against
      NGF

<400> SEQUENCE: 52
gggagaacuu cgaccagaag uuugaaaaaa acccaaauua aaguaugugc gcauaca     57

<210> SEQ ID NO 53
<211> LENGTH: 56
<212> TYPE: RNA
<213> ORGANISM: Artificial
<220> FEATURE:
<223> OTHER INFORMATION: nucleic acid having binding activity against
      NGF

<400> SEQUENCE: 53
gggagaacuu cgaccagagu cgagagcgaa agaaacuccc aaauaugugc gcauac      56

<210> SEQ ID NO 54
<211> LENGTH: 58
<212> TYPE: RNA
<213> ORGANISM: Artificial
<220> FEATURE:
<223> OTHER INFORMATION: nucleic acid having binding activity against
```

NGF

<400> SEQUENCE: 54
gggagaacuu cgaccagaag auuugaaaaa aacccaaauu aaaguaugug cgcauaca       58

<210> SEQ ID NO 55
<211> LENGTH: 41
<212> TYPE: RNA
<213> ORGANISM: Artificial
<220> FEATURE:
<223> OTHER INFORMATION: nucleic acid having binding activity against
      NGF

<400> SEQUENCE: 55
gggauaaaaa uagaguuuga uaaacaccug uauuaaaacc c       41

<210> SEQ ID NO 56
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 56
gggauaaaaa uagaguuuga taaacaccug uauuaaaacc c       41

<210> SEQ ID NO 57
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 57
gggauaaaaa uagagtuuga taaacaccug uauuaaaacc c       41

<210> SEQ ID NO 58
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 58
gggauaaaaa uagaguuuga taaacaccug uautaaaacc c       41

<210> SEQ ID NO 59
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 59
gggauaaaaa uagaguuuga taaacaccug uauuaaaacc c       41

<210> SEQ ID NO 60
<211> LENGTH: 41
<212> TYPE: DNA
<213> ORGANISM: Artificial
<220> FEATURE:
<223> OTHER INFORMATION: nucleic acid having binding activity against
      NGF

```
<400> SEQUENCE: 60
gggauaaaaa uagaguuuga tauacaccug uauuaaaacc c                    41

<210> SEQ ID NO 61
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 61
gggauaaaaa uagaguuuga taaacaccug uauuaaaacc c                    41

<210> SEQ ID NO 62
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 62
gggauaaaaa uagaguuuga taaacaccug uauuaaaacc c                    41

<210> SEQ ID NO 63
<211> LENGTH: 41
<212> TYPE: DNA
<213> ORGANISM: Artificial
<220> FEATURE:
<223> OTHER INFORMATION: nucleic acid having binding activity against
      NGF

<400> SEQUENCE: 63
gggauaaaaa uagaguuuga taaacaccug uauuaaaacc c                    41

<210> SEQ ID NO 64
<211> LENGTH: 11
<212> TYPE: RNA
<213> ORGANISM: Artificial
<220> FEATURE:
<223> OTHER INFORMATION: consensus sequence

<400> SEQUENCE: 64
ugaaaraaac c                                                     11

<210> SEQ ID NO 65
<211> LENGTH: 11
<212> TYPE: RNA
<213> ORGANISM: Artificial
<220> FEATURE:
<223> OTHER INFORMATION: consensus sequence

<400> SEQUENCE: 65
cgaamraaac u                                                     11

<210> SEQ ID NO 66
<211> LENGTH: 11
<212> TYPE: RNA
<213> ORGANISM: Artificial
<220> FEATURE:
<223> OTHER INFORMATION: consensus sequence

<400> SEQUENCE: 66
ugaaaaaaac c                                                     11
```

```
<210> SEQ ID NO 67
<211> LENGTH: 11
<212> TYPE: RNA
<213> ORGANISM: Artificial
<220> FEATURE:
<223> OTHER INFORMATION: consensus sequence

<400> SEQUENCE: 67
ugaaagaaac c                                                              11

<210> SEQ ID NO 68
<211> LENGTH: 11
<212> TYPE: RNA
<213> ORGANISM: Artificial
<220> FEATURE:
<223> OTHER INFORMATION: consensus sequence

<400> SEQUENCE: 68
cgaacaaaac u                                                              11

<210> SEQ ID NO 69
<211> LENGTH: 11
<212> TYPE: RNA
<213> ORGANISM: Artificial
<220> FEATURE:
<223> OTHER INFORMATION: consensus sequence

<400> SEQUENCE: 69
cgaaagaaac u                                                              11

<210> SEQ ID NO 70
<211> LENGTH: 86
<212> TYPE: DNA
<213> ORGANISM: Artificial
<220> FEATURE:
<223> OTHER INFORMATION: selected NGF DNA Aptamer from WO 02/077262
<220> FEATURE:
<221> NAME/KEY: misc_feature
<222> LOCATION: (2)..(2)
<223> OTHER INFORMATION: n is 5-bromo-2?-deoxyuridine
<220> FEATURE:
<221> NAME/KEY: misc_feature
<222> LOCATION: (4)..(4)
<223> OTHER INFORMATION: n is 5-bromo-2?-deoxyuridine
<220> FEATURE:
<221> NAME/KEY: misc_feature
<222> LOCATION: (6)..(6)
<223> OTHER INFORMATION: n is 5-bromo-2?-deoxyuridine
<220> FEATURE:
<221> NAME/KEY: misc_feature
<222> LOCATION: (8)..(8)
<223> OTHER INFORMATION: n is 5-bromo-2?-deoxyuridine
<220> FEATURE:
<221> NAME/KEY: misc_feature
<222> LOCATION: (19)..(19)
<223> OTHER INFORMATION: n is 5-bromo-2?-deoxyuridine
<220> FEATURE:
<221> NAME/KEY: misc_feature
<222> LOCATION: (30)..(30)
<223> OTHER INFORMATION: n is 5-bromo-2?-deoxyuridine
<220> FEATURE:
<221> NAME/KEY: misc_feature
<222> LOCATION: (31)..(31)
<223> OTHER INFORMATION: n is 5-bromo-2?-deoxyuridine
<220> FEATURE:
<221> NAME/KEY: misc_feature
<222> LOCATION: (35)..(35)
<223> OTHER INFORMATION: n is 5-bromo-2?-deoxyuridine
<220> FEATURE:
<221> NAME/KEY: misc_feature
<222> LOCATION: (40)..(40)
```

<223> OTHER INFORMATION: n is 5-bromo-2?-deoxyuridine
<220> FEATURE:
<221> NAME/KEY: misc_feature
<222> LOCATION: (41)..(41)
<223> OTHER INFORMATION: n is 5-bromo-2?-deoxyuridine
<220> FEATURE:
<221> NAME/KEY: misc_feature
<222> LOCATION: (46)..(46)
<223> OTHER INFORMATION: n is 5-bromo-2?-deoxyuridine
<220> FEATURE:
<221> NAME/KEY: misc_feature
<222> LOCATION: (47)..(47)
<223> OTHER INFORMATION: n is 5-bromo-2?-deoxyuridine
<220> FEATURE:
<221> NAME/KEY: misc_feature
<222> LOCATION: (52)..(52)
<223> OTHER INFORMATION: n is 5-bromo-2?-deoxyuridine
<220> FEATURE:
<221> NAME/KEY: misc_feature
<222> LOCATION: (53)..(53)
<223> OTHER INFORMATION: n is 5-bromo-2?-deoxyuridine
<220> FEATURE:
<221> NAME/KEY: misc_feature
<222> LOCATION: (56)..(56)
<223> OTHER INFORMATION: n is 5-bromo-2?-deoxyuridine
<220> FEATURE:
<221> NAME/KEY: misc_feature
<222> LOCATION: (57)..(57)
<223> OTHER INFORMATION: n is 5-bromo-2?-deoxyuridine
<220> FEATURE:
<221> NAME/KEY: misc_feature
<222> LOCATION: (58)..(58)
<223> OTHER INFORMATION: n is 5-bromo-2?-deoxyuridine
<220> FEATURE:
<221> NAME/KEY: misc_feature
<222> LOCATION: (60)..(60)
<223> OTHER INFORMATION: n is 5-bromo-2?-deoxyuridine
<220> FEATURE:
<221> NAME/KEY: misc_feature
<222> LOCATION: (62)..(62)
<223> OTHER INFORMATION: n is 5-bromo-2?-deoxyuridine

<400> SEQUENCE: 70
anananangg gaggacgang cgggcacacn naaanccacn ncaccnnaca anncnnnan    60 cngcagacga cgagcgggaa aaaaaa                                       86

<210> SEQ ID NO 71
<211> LENGTH: 86
<212> TYPE: DNA
<213> ORGANISM: Artificial
<220> FEATURE:
<223> OTHER INFORMATION: selected NGF DNA Aptamer from WO 02/077262
<220> FEATURE:
<221> NAME/KEY: misc_feature
<222> LOCATION: (2)..(2)
<223> OTHER INFORMATION: n is 5-bromo-2?-deoxyuridine
<220> FEATURE:
<221> NAME/KEY: misc_feature
<222> LOCATION: (4)..(4)
<223> OTHER INFORMATION: n is 5-bromo-2?-deoxyuridine
<220> FEATURE:
<221> NAME/KEY: misc_feature
<222> LOCATION: (6)..(6)
<223> OTHER INFORMATION: n is 5-bromo-2?-deoxyuridine
<220> FEATURE:
<221> NAME/KEY: misc_feature
<222> LOCATION: (8)..(8)
<223> OTHER INFORMATION: n is 5-bromo-2?-deoxyuridine
<220> FEATURE:
<221> NAME/KEY: misc_feature
<222> LOCATION: (19)..(19)
<223> OTHER INFORMATION: n is 5-bromo-2?-deoxyuridine
<220> FEATURE:
<221> NAME/KEY: misc_feature
<222> LOCATION: (35)..(35)
<223> OTHER INFORMATION: n is 5-bromo-2?-deoxyuridine

```
<220> FEATURE:
<221> NAME/KEY: misc_feature
<222> LOCATION: (36)..(36)
<223> OTHER INFORMATION: n is 5-bromo-2?-deoxyuridine
<220> FEATURE:
<221> NAME/KEY: misc_feature
<222> LOCATION: (38)..(38)
<223> OTHER INFORMATION: n is 5-bromo-2?-deoxyuridine
<220> FEATURE:
<221> NAME/KEY: misc_feature
<222> LOCATION: (39)..(39)
<223> OTHER INFORMATION: n is 5-bromo-2?-deoxyuridine
<220> FEATURE:
<221> NAME/KEY: misc_feature
<222> LOCATION: (42)..(42)
<223> OTHER INFORMATION: n is 5-bromo-2?-deoxyuridine
<220> FEATURE:
<221> NAME/KEY: misc_feature
<222> LOCATION: (44)..(44)
<223> OTHER INFORMATION: n is 5-bromo-2?-deoxyuridine
<220> FEATURE:
<221> NAME/KEY: misc_feature
<222> LOCATION: (46)..(46)
<223> OTHER INFORMATION: n is 5-bromo-2?-deoxyuridine
<220> FEATURE:
<221> NAME/KEY: misc_feature
<222> LOCATION: (47)..(47)
<223> OTHER INFORMATION: n is 5-bromo-2?-deoxyuridine
<220> FEATURE:
<221> NAME/KEY: misc_feature
<222> LOCATION: (48)..(48)
<223> OTHER INFORMATION: n is 5-bromo-2?-deoxyuridine
<220> FEATURE:
<221> NAME/KEY: misc_feature
<222> LOCATION: (58)..(58)
<223> OTHER INFORMATION: n is 5-bromo-2?-deoxyuridine
<220> FEATURE:
<221> NAME/KEY: misc_feature
<222> LOCATION: (59)..(59)
<223> OTHER INFORMATION: n is 5-bromo-2?-deoxyuridine
<220> FEATURE:
<221> NAME/KEY: misc_feature
<222> LOCATION: (62)..(62)
<223> OTHER INFORMATION: n is 5-bromo-2?-deoxyuridine

<400> SEQUENCE: 71 ananaangg gaggacgang cgggcccaa acacnngnnc cnancnnnca acccccnng      60 anccagacga cgagcgggaa aaaaaa                                        86

<210> SEQ ID NO 72
<211> LENGTH: 11
<212> TYPE: RNA
<213> ORGANISM: Artificial
<220> FEATURE:
<223> OTHER INFORMATION: conserved portion of SEQ ID NO: 26

<400> SEQUENCE: 72
ugaaagaaac c                                                        11
```